(12) United States Patent
Ruiz-Opazo et al.

(10) Patent No.: US 6,844,483 B2
(45) Date of Patent: Jan. 18, 2005

(54) METHOD OF ASSAYING MODULATORS OF HYPERTENSION

(75) Inventors: Nelson Ruiz-Opazo, Westwood, MA (US); Victoria L. M. Herrera, Westwood, MA (US)

(73) Assignee: NoMI LLC, Wellesley, MA (US)

( * ) Notice: Subject to any disclaimer, the term of this patent is extended or adjusted under 35 U.S.C. 154(b) by 0 days.

(21) Appl. No.: 10/040,722

(22) Filed: Jan. 7, 2002

(65) Prior Publication Data

US 2002/0095691 A1 Jul. 18, 2002

Related U.S. Application Data

(63) Continuation of application No. 09/653,030, filed on Sep. 1, 2000, now abandoned.
(60) Provisional application No. 60/152,011, filed on Sep. 1, 1999.

(51) Int. Cl.[7] ................................................ G01N 33/00
(52) U.S. Cl. ............................................. 800/3; 424/9.2
(58) Field of Search ........................... 800/3, 8, 14, 13, 800/21, 9, 18; 424/9.2, 9.1

(56) References Cited

U.S. PATENT DOCUMENTS 5,691,310 A * 11/1997 Vesely .......................... 514/12

OTHER PUBLICATIONS

VLM Herrera et al., Science, "Alteration of α1 Na+, K+–aTPase 86Rb+ Influx by a Single Amino Acid Substitution," 1990, vol. 249, pp. 1023–1026.*
RJ Wall, Theriogenology, "Transgenic Livestock: Progress and Prospects for the Future," 1996, 45:57–68.*
LJ Mullins et al., J Clin. Invest., "Perspectives Series:Molecular Medicine in Genetically Engineered Animals." Apr. 1996, vol. 97, No. 7, pp. 1557–1560.*
IA Polejaeva et al., Theriogenology, "New Advances in Somatic Cell Nuclear Transfer: Application in Transgenesis," 2000. 53:117–126.*
JO Bishop, Repro Nutr Dev. "Chromosomal insertion of foreign DNA," 1996, 36, pp. 607–618.*
L–M Houdebine, Journal of Biotechnology, "Production of pharmaceutical proteins from transgenic animals,"1994, 34: pp. 269–287.*
T Rulicke et al., Experimental Physiology,"Germ line transformation of mammals by pronuclear microinjection," 2000, 085.6,pp. 589–601*
RM Strojek et al., Genetic Engineering: Principles and methods, Plenum Press, 1988, vol. 10, pp. 221–246.*
L Somova et al., Methods Find Exp Clin Pharmacol., "Glucose Metabolism and Insulin Sensitivity in Dahl Hypertensive Rats," 1999, 21(6) pp. 421–425.*
OS Medvedev et al., Journal of Autonomic Nervous System, "Chronopharmacological dependence of antihypertensive effects of the imidazoline–like drugs in stroke–prone spontaneously hypertensive rats," 1998, 72, pp. 170–176.*

P Hamet et al., Journal of Hypertension, "Hypertension: Genes and environment," 1998, vol. 16, pp. 397–418.*
VLM Herrera et al., J Clin Invest., "The a 1 Na, K–ATPase Gene is a Susceptibility Hypertension Gene in the Dahl Salt–Sensitive HSD Rat," Sep. 1998, vol. 102, No. 6, pp. 1102–1111.*
N Ruiz–Opazo et al., Hypertension, "Pressure–Overload Deinduction of Human a2,Na,K–ATPase Gene Expression in Transgenic Rats," 1997, 29: 606–612.
Culter Linder, Lab Animal, vol. 30, pp. 34–39, 2001.*
Sigmund, Arterioscler Thromb Vasc Bio. vol. 20:1425–1429, 2000.*
Canessa et al., "The α1 Na(+)–K+ Pump of the Dahl Salt–Sensitive Rat Exhibits Altered $Na^+$ Modulation of $K^+$ Transport in Red Blood Cells," J. Membr. Biol 134: 107–122, 1993.
Clark et al., "Quantitative Trait Loci in Genetically Hypertensive Rats. Possible Sex Specificity," Hypertension 28: 898–906, 1996.
Dallner, "Isolation of Rough and Smooth Microsome—General," In Methods in Enzymology, vol. XXXI, S. Fleischer and L. Packer, editors, Academic Press, New York, 31:191–201, 1974.
Deng et al., "Mapping of a Quantitative Trait Locus for Blood Pressure on Rat Chromosome 2," J. Clin. Invest. 94:431–436, 1994.
de Wardener, H.E., The Primary Role of the Kidney and Salt Intake in the Aetiology of Essential Hypertension, Part II, Clin. Sci. 79: 289–297, 1990.
Dubay, C. et al., "Genetic Determinants of Diastolic and Pulse Pressure Map to Different Loci in Lyon Hypertensive Rats," Nat. Genet. 3: 354–357, 1993.
Goldman, "High Anxiety," Science 274: 1483, 1996.
Herrera and Ruiz–Opazo "Beyond Genetic Markers: Hypertension Genes," J. Hypertension 12: 847–856, 1994.
Herrera et al., "Developmental Cell–Specific Regulation of Na(+)–K(+)–ATPase α1–, α2–, and α3–isoform gene expression," Am. J. Physiol. 266: C1301–C1312, 1994.
Jacob et al., "A Genetic Linkage Map of the Laboratory Rat, Rattus Norvegicus," Nat. Genet 9: 63–69, 1995.
Lander and Kruglyak, "Genetic Dissection of Complex Traits: Guidlines for Interpreting and Reporting Linkage Results," Nat. Genet. 11:241–247, 1995.
Lesch et al., "Association of Anxiety–Related Traits with a Polymorphism in the Serotonin Transporter Gene Regulatory Region," Science 274: 1527–1531, 1996.

(List continued on next page.)

Primary Examiner—Scott D. Priebe
Assistant Examiner—Brian Whiteman
(74) Attorney, Agent, or Firm—Paul T. Clark; Clark & Elbing LLP

(57) ABSTRACT

The invention features methods for assaying compounds that affect hypertension by using an animal model with a functionally variant hypertension susceptibility gene.

2 Claims, 5 Drawing Sheets

OTHER PUBLICATIONS

Lewis et al., "Analysis of the Genetic Contamination of Salt–Sensitive Dahl/Rapp Rats," *Hypertension* 24: 255–259, 1994.

Orosz and Hopfer, "Pathophysiologic Consequences of Changes in the Coupling Ratio of Na,K–ATPase for Renal Sodium Reabsorption and its Implications for Hypertension," *Hypertension* 27:219–227, 1996.

Raij et al., "Mesangial Immune Injury, Hypertension, and Progressive Glomerular Damage in Dahl Rats," *Kidney Int.* 26: 137–143, 1984.

Rapp and Dene, "Development and Characteristics of Inbred Stains of Dahl Salt–Sensitive and Salt–Resistant Rats," *Hypertension* 7: 340–349, 1985.

Ruiz–Opazo et al., "Confirmation of Mutant α1 Na,K–ATPase Gene and Transcript in Dahl Salt–Sensitive/JR Rats," *Hypertension* 24:260–270, 1994.

Ruiz–Opazo et al, "Characterization of a Sodium–Response Transcriptional Mechanism," *Hypertension* 30: 191–198, 1997.

Samani et al., "Analysis of Quantitative Trait Loci for Blood Pressure on Rat Chromosomes 2 and 13. Age–Related Differences in Effect," *Hypertension* 28: 1118–1122, 1996.

Shull et al., "Molecular Cloning of Three Distinct Forms of the Na+,K+–ATPase αSubunit From Rat Brain," *Biochemistry* 25 8125–8132, 1986.

Simonet et al., "Sequence Analysis of the α1 Na+, K+–ATPase Gene in the Dahl Salt–Sensitive Rat," *Hypertension* 18:689–693, 1991.

St. Lezin et al., "Genetic Contamination of Dahl SS/JR Rats: Impacts on Studies of Salt–Sensitive Hypertension," *Hypertension* 23: 786–790, 1994.

* cited by examiner

FIG. 4A
FIG. 4B
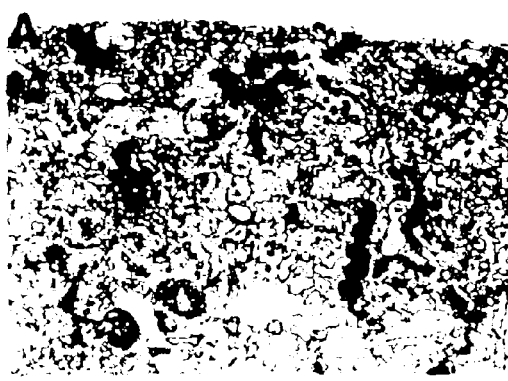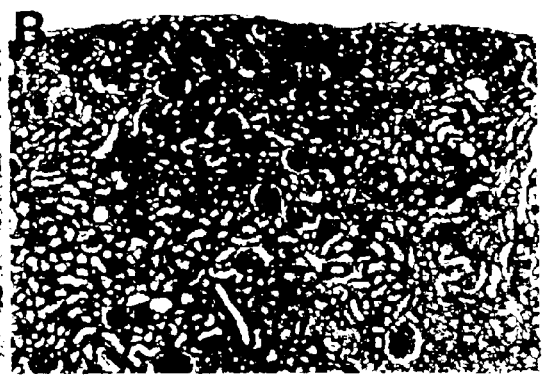
FIG. 4C
FIG. 4D
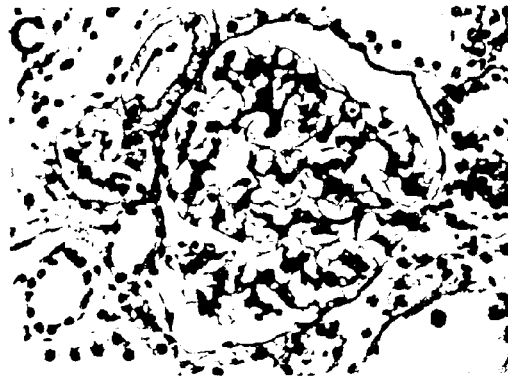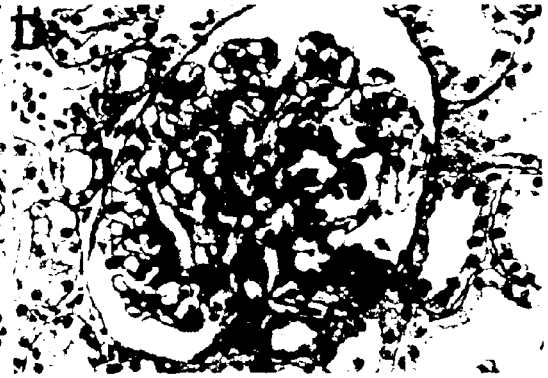
FIG. 4E  FIG. 4F  FIG. 4G
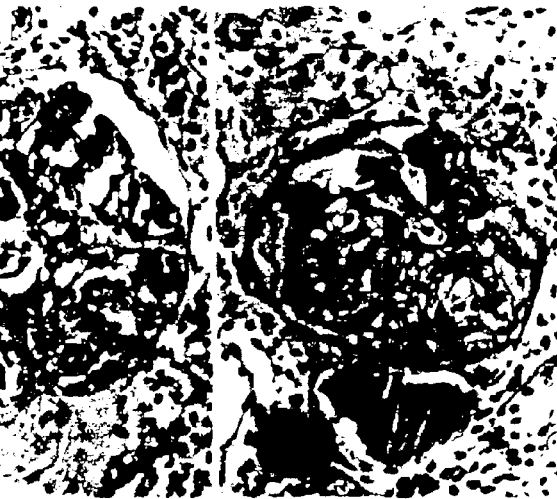

SEQUENCE LISTING

```
<160> NUMBER OF SEQ ID NOS: 4

<210> SEQ ID NO 1
<211> LENGTH: 3636
<212> TYPE: DNA
<213> ORGANISM: Rattus norvegicus
<220> FEATURE:
<221> NAME/KEY: CDS
<222> LOCATION: (238)...(3309)

<400> SEQUENCE: 1
ggagcctcgg cgggaggagg cggacacgtg gcagcggcgg cggcagcggc agcagcagcg      60
gcggcagcag cggcggcctc ggtccggggc gccggccgtc ctccctcttt cctccggcgg     120
cagccctagt tcccgcctct cggctccccc ggctccactc tcccagccgg gagctgctct     180
ctcctctttc tagtctccag ccacaggacc cggcgcgggg cccgcagcgc cgccacc atg    240
                                                                     Met
```

```
                                                                     1
ggg aag ggg gtt gga cga gac aag tat gag ccc gca gct gta tca gaa      288
Gly Lys Gly Val Gly Arg Asp Lys Tyr Glu Pro Ala Ala Val Ser Glu
        5                   10                  15 cat ggg gac aag aag agc aag aag gcg aag aag gaa agg gac atg gac      336
His Gly Asp Lys Lys Ser Lys Lys Ala Lys Lys Glu Arg Asp Met Asp
        20                  25                  30 gaa ctc aag aag gaa gtg tct atg gac gac cat aaa ctc agc ctg gat      384
Glu Leu Lys Lys Glu Val Ser Met Asp Asp His Lys Leu Ser Leu Asp
35                  40                  45 gaa ctc cat cgt aaa tac gga aca gat ttg agc cga ggc cta aca ccc      432
Glu Leu His Arg Lys Tyr Gly Thr Asp Leu Ser Arg Gly Leu Thr Pro
50                  55                  60                  65 gca agg gcc gct gag atc ctg gct cgg gat ggc ccc aac gcc ctc acg      480
Ala Arg Ala Ala Glu Ile Leu Ala Arg Asp Gly Pro Asn Ala Leu Thr
                70                  75                  80 ccc cct ccc act act ccc gag tgg gtc aaa ttc tgt cgg cag ctg ttc      528
Pro Pro Pro Thr Thr Pro Glu Trp Val Lys Phe Cys Arg Gln Leu Phe
                85                  90                  95 ggt ggc ttc tcc atg tta ctg tgg att gga gcc att ctt tgt ttc ttg      576
Gly Gly Phe Ser Met Leu Leu Trp Ile Gly Ala Ile Leu Cys Phe Leu
            100                 105                 110 gct tat ggc atc cga agt gct aca gaa gag gaa cca cca aat gat gat      624
Ala Tyr Gly Ile Arg Ser Ala Thr Glu Glu Glu Pro Pro Asn Asp Asp
115                 120                 125 ctg tac ctc ggg gtc gtg ctg tct gct gtc gtc atc ata act ggc tgt      672
Leu Tyr Leu Gly Val Val Leu Ser Ala Val Val Ile Ile Thr Gly Cys
130                 135                 140                 145 ttc tcc tat tat caa gaa gca aaa agc tcc aag atc atg gaa tcc ttc      720
Phe Ser Tyr Tyr Gln Glu Ala Lys Ser Ser Lys Ile Met Glu Ser Phe
                150                 155                 160 aag aac atg gtc cct cag caa gcc ctc gtg att cga aat gga gag aag      768
Lys Asn Met Val Pro Gln Gln Ala Leu Val Ile Arg Asn Gly Glu Lys
            165                 170                 175 atg agc atc aac gca gag gat gtc gtc gtt ggt gat ctg gtg gag gtg      816
Met Ser Ile Asn Ala Glu Asp Val Val Val Gly Asp Leu Val Glu Val
        180                 185                 190 aag ggc gga gac cga atc cct gct gat ctc aga atc ata tct gca aat      864
Lys Gly Gly Asp Arg Ile Pro Ala Asp Leu Arg Ile Ile Ser Ala Asn
195                 200                 205 ggc tgc aag gtg gat aac tcc tca ctc act ggt gaa tca gaa ccc cag      912
Gly Cys Lys Val Asp Asn Ser Ser Leu Thr Gly Glu Ser Glu Pro Gln
210                 215                 220                 225 act cgg tcc ccg gat ttc aca aac gag aac ccc ttg gag aca agg aac      960
Thr Arg Ser Pro Asp Phe Thr Asn Glu Asn Pro Leu Glu Thr Arg Asn
                230                 235                 240 att gcc ttc ttc tca acc aac tgt gtt gaa gga act gca cgt ggc atc      1008
Ile Ala Phe Phe Ser Thr Asn Cys Val Glu Gly Thr Ala Arg Gly Ile
            245                 250                 255 gtt gtg tac act ggg gat cgc acc gtg atg ggc agg atc gcc acc ctt      1056
Val Val Tyr Thr Gly Asp Arg Thr Val Met Gly Arg Ile Ala Thr Leu
        260                 265                 270 gct tct ggg ctg gaa ggc ggc cag acc ccc att gct gaa gaa atc gag      1104
Ala Ser Gly Leu Glu Gly Gly Gln Thr Pro Ile Ala Glu Glu Ile Glu
275                 280                 285 cac ttc atc cac ctc atc acg ggt gtg gcc gtg ttc ctg ggg gtg tct      1152
His Phe Ile His Leu Ile Thr Gly Val Ala Val Phe Leu Gly Val Ser
290                 295                 300                 305 ttc ttc att ctc tct ctg atc ctt gag tac acc tgg ctc gag gct gtc      1200
```

```
                Phe Phe Ile Leu Ser Leu Ile Leu Glu Tyr Thr Trp Leu Glu Ala Val
                                310                 315                 320 atc ttc ctc att ggt atc atc gta gcc aac gtg ccg gaa ggt ttg ctg          1248
Ile Phe Leu Ile Gly Ile Ile Val Ala Asn Val Pro Glu Gly Leu Leu
            325                 330                 335 gcc acc gtc acg gta tgt ctg acg ctc act gcc aag cgc atg gcg agg          1296
Ala Thr Val Thr Val Cys Leu Thr Leu Thr Ala Lys Arg Met Ala Arg
            340                 345                 350 aag aac tgc ctg gtg aag aac ctg gaa gct gtg gag acc ttg ggg tcc          1344
Lys Asn Cys Leu Val Lys Asn Leu Glu Ala Val Glu Thr Leu Gly Ser
            355                 360                 365 aca tcc acc atc tgc tcc gac aag act gga act ctg act cag aac cgg          1392
Thr Ser Thr Ile Cys Ser Asp Lys Thr Gly Thr Leu Thr Gln Asn Arg
370             375                 380                 385 atg aca gtg gct cac atg tgg ttt gac aat caa atc cat gaa gct gac          1440
Met Thr Val Ala His Met Trp Phe Asp Asn Gln Ile His Glu Ala Asp
                390                 395                 400 acc aca gag aat cag agt ggg gtc tcc ttt gac aag acg tca gcc acc          1488
Thr Thr Glu Asn Gln Ser Gly Val Ser Phe Asp Lys Thr Ser Ala Thr
                405                 410                 415 tgg ttc gct ctg tcc aga att gct ggt ctc tgt aac agg gca gtg ttt          1536
Trp Phe Ala Leu Ser Arg Ile Ala Gly Leu Cys Asn Arg Ala Val Phe
            420                 425                 430 cag gct aac caa gaa aac ctg cct atc ctt aag cgt gca gta gcg gga          1584
Gln Ala Asn Gln Glu Asn Leu Pro Ile Leu Lys Arg Ala Val Ala Gly
            435                 440                 445 gat gct tcc gag tcg gcg ctc tta aag tgc atc gag gtc tgc tgt ggc          1632
Asp Ala Ser Glu Ser Ala Leu Leu Lys Cys Ile Glu Val Cys Cys Gly
450             455                 460                 465 tcc gtg atg gag atg agg gag aag tac acc aag ata gtg gag att cct          1680
Ser Val Met Glu Met Arg Glu Lys Tyr Thr Lys Ile Val Glu Ile Pro
                470                 475                 480 ttc aac tcc acc aac aag tac cag ctc tcc att cac aag aac cca aac          1728
Phe Asn Ser Thr Asn Lys Tyr Gln Leu Ser Ile His Lys Asn Pro Asn
                485                 490                 495 gca tcg gag cct aag cac ctg cta gtg atg aag ggc gcc cca gaa agg          1776
Ala Ser Glu Pro Lys His Leu Leu Val Met Lys Gly Ala Pro Glu Arg
            500                 505                 510 atc ctg gac cga tgc agt tct atc ctc ctc cac ggc aag gag cag ccc          1824
Ile Leu Asp Arg Cys Ser Ser Ile Leu Leu His Gly Lys Glu Gln Pro
515             520                 525 ctg gac gaa gag ctg aag gac gcc ttt cag aat gcc tac cta gag ctg          1872
Leu Asp Glu Glu Leu Lys Asp Ala Phe Gln Asn Ala Tyr Leu Glu Leu
530             535                 540                 545 ggg ggc ctt gga gag cgt gtg cta ggt ttc tgc cac ctc ctt ctg cct          1920
Gly Gly Leu Gly Glu Arg Val Leu Gly Phe Cys His Leu Leu Leu Pro
                550                 555                 560 gac gaa cag ttt ccc gaa ggc ttc cag ttt gac act gat gaa gtc aat          1968
Asp Glu Gln Phe Pro Glu Gly Phe Gln Phe Asp Thr Asp Glu Val Asn
                565                 570                 575 ttc ccc gtg gat aac ctc tgc ttc gtg ggt ctt atc tcc atg att gac          2016
Phe Pro Val Asp Asn Leu Cys Phe Val Gly Leu Ile Ser Met Ile Asp
            580                 585                 590 cct cct cga gct gct gtc ccc gat gct gtg ggc aaa tgc cgc agc gct          2064
Pro Pro Arg Ala Ala Val Pro Asp Ala Val Gly Lys Cys Arg Ser Ala
            595                 600                 605 ggg att aag gtc atc atg gtc aca gga gac cat cca atc aca gcc aaa          2112
Gly Ile Lys Val Ile Met Val Thr Gly Asp His Pro Ile Thr Ala Lys
610             615                 620                 625
```

-continued

```
gcc att gct aag ggg gtg ggc att atc tca gaa ggt aac gag acc gtg      2160
Ala Ile Ala Lys Gly Val Gly Ile Ile Ser Glu Gly Asn Glu Thr Val
            630                 635                 640 gaa gac att gct gcc cgc ctc aac att cca gtg aac cag gtg aac ccc      2208
Glu Asp Ile Ala Ala Arg Leu Asn Ile Pro Val Asn Gln Val Asn Pro
                645                 650                 655 aga gat gcc aag gcc tgt gta gta cat ggc agt gac ttg aag gac atg      2256
Arg Asp Ala Lys Ala Cys Val Val His Gly Ser Asp Leu Lys Asp Met
            660                 665                 670 acc tct gag gag ctg gat gac att ttg cgg tac cac acg gag att gtc      2304
Thr Ser Glu Glu Leu Asp Asp Ile Leu Arg Tyr His Thr Glu Ile Val
675                 680                 685 ttt gct agg acc tct cct caa cag aag ctc atc att gtg gag ggc tgc      2352
Phe Ala Arg Thr Ser Pro Gln Gln Lys Leu Ile Ile Val Glu Gly Cys
690                 695                 700                 705 cag cgg cag ggt gcc atc gtg gct gtc aca ggg gat ggt gtc aat gac      2400
Gln Arg Gln Gly Ala Ile Val Ala Val Thr Gly Asp Gly Val Asn Asp
                710                 715                 720 tct cca gct ttg aaa aag gca gat att ggg gtt gcc atg ggg att gtt      2448
Ser Pro Ala Leu Lys Lys Ala Asp Ile Gly Val Ala Met Gly Ile Val
                725                 730                 735 ggc tcg gat gtg tcc aag caa gct gct gac atg att ctt ctg gat gac      2496
Gly Ser Asp Val Ser Lys Gln Ala Ala Asp Met Ile Leu Leu Asp Asp
            740                 745                 750 aac ttt gcc tcc atc gtg act gga gta gaa gaa ggt cgt ctg ata ttt      2544
Asn Phe Ala Ser Ile Val Thr Gly Val Glu Glu Gly Arg Leu Ile Phe
            755                 760                 765 gat aac ttg aag aaa tcc att gct tac acc cta aca agt aac att ccg      2592
Asp Asn Leu Lys Lys Ser Ile Ala Tyr Thr Leu Thr Ser Asn Ile Pro
770                 775                 780                 785 gaa atc acc ccc ttc ttg ata ttt att att gca aac att cca ctg ccc      2640
Glu Ile Thr Pro Phe Leu Ile Phe Ile Ile Ala Asn Ile Pro Leu Pro
                790                 795                 800 ctg ggc acc gtg acc atc ctc tgc att gac ttg ggc act gac atg gtt      2688
Leu Gly Thr Val Thr Ile Leu Cys Ile Asp Leu Gly Thr Asp Met Val
                805                 810                 815 ccc gcc atc tct ctg gcc tat gaa cag gct gaa agt gac atc atg aag      2736
Pro Ala Ile Ser Leu Ala Tyr Glu Gln Ala Glu Ser Asp Ile Met Lys
            820                 825                 830 agg cag ccc aga aat ccc aaa acg gac aaa ctt gtg aac gag cgt ctg      2784
Arg Gln Pro Arg Asn Pro Lys Thr Asp Lys Leu Val Asn Glu Arg Leu
835                 840                 845 atc agc atg gcc tat gga cag atc ggt atg atc cag gcc ctg gga ggc      2832
Ile Ser Met Ala Tyr Gly Gln Ile Gly Met Ile Gln Ala Leu Gly Gly
850                 855                 860                 865 ttc ttc act tat ttt gtg att ctg gct gag aac ggt ttc ctg ccc ttt      2880
Phe Phe Thr Tyr Phe Val Ile Leu Ala Glu Asn Gly Phe Leu Pro Phe
                870                 875                 880 cac ctg ttg ggc atc cga gag acc tgg gat gac cgc tgg atc aat gat      2928
His Leu Leu Gly Ile Arg Glu Thr Trp Asp Asp Arg Trp Ile Asn Asp
            885                 890                 895 gtg gag gac agc tac ggg cag cag tgg acc tac gag cag agg aag att      2976
Val Glu Asp Ser Tyr Gly Gln Gln Trp Thr Tyr Glu Gln Arg Lys Ile
            900                 905                 910 gtg gag ttc acc tgc cac acg gcc ttc ttt gtc agt atc gtg gta gtg      3024
Val Glu Phe Thr Cys His Thr Ala Phe Phe Val Ser Ile Val Val Val
            915                 920                 925 cag tgg gct gac ttg gtc atc tgc aag acc aga agg aat tct gtc ttc      3072
Gln Trp Ala Asp Leu Val Ile Cys Lys Thr Arg Arg Asn Ser Val Phe
930                 935                 940                 945
```

-continued

```
cag cag gga atg aag aac aag atc tta ata ttt ggc ctc ttt gaa gag     3120
Gln Gln Gly Met Lys Asn Lys Ile Leu Ile Phe Gly Leu Phe Glu Glu
            950                 955                 960 aca gct ctt gct gct ttc ctg tcc tac tgc cct ggg atg ggt gca gcc     3168
Thr Ala Leu Ala Ala Phe Leu Ser Tyr Cys Pro Gly Met Gly Ala Ala
        965                 970                 975 ctt agg atg tat ccc ctc aaa cct act tgg tgg ttc tgt gcc ttc ccc     3216
Leu Arg Met Tyr Pro Leu Lys Pro Thr Trp Trp Phe Cys Ala Phe Pro
    980                 985                 990 tac tcc ctt ctc atc ttc gtg tat gac gag gtg cgg aag ctc atc atc     3264
Tyr Ser Leu Leu Ile Phe Val Tyr Asp Glu Val Arg Lys Leu Ile Ile
995                 1000                1005 agg cga cgc cct ggc ggc tgg gtg gag aag gaa acc tac tac tag         3309
Arg Arg Arg Pro Gly Gly Trp Val Glu Lys Glu Thr Tyr Tyr *
1010                1015                1020 cccactgccc tgcacgccgt ggaacattgt gccacacact gcacctaccc ctaccccccc   3369
tttgtgtact tcaagtcttg gagctcggaa ctctaccctg gtaggaaagc accaaagcat   3429
gtggggatcc agacgtcctg gaatgaagca tgtagctgta atgggggcg ggggagggc     3489 tgcccgaaaa acaccgtgga cggggacgac agcggggaag gtttatatgt gcctttttgt   3549
ttttgtaaaa aaggaaaaacc tggaaagact gaaagattac gttttatatc tggatttta   3609 caaataaaga tggctattat aacggaa                                       3636
```

<210> SEQ ID NO 2
<211> LENGTH: 1023
<212> TYPE: PRT
<213> ORGANISM: Rattus norvegicus

<400> SEQUENCE: 2

```
Met Gly Lys Gly Val Gly Arg Asp Lys Tyr Glu Pro Ala Ala Val Ser
 1               5                  10                  15

Glu His Gly Asp Lys Lys Ser Lys Lys Ala Lys Lys Glu Arg Asp Met
            20                  25                  30

Asp Glu Leu Lys Lys Glu Val Ser Met Asp Asp His Lys Leu Ser Leu
        35                  40                  45

Asp Glu Leu His Arg Lys Tyr Gly Thr Asp Leu Ser Arg Gly Leu Thr
    50                  55                  60

Pro Ala Arg Ala Ala Glu Ile Leu Ala Arg Asp Gly Pro Asn Ala Leu
65                  70                  75                  80

Thr Pro Pro Pro Thr Thr Pro Glu Trp Val Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Gly Ile Arg Ser Ala Thr Glu Glu Glu Pro Pro Asn Asp
        115                 120                 125

Asp Leu Tyr Leu Gly Val Val Leu Ser Ala Val Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Asp Val Val Gly Asp Leu Val Glu
            180                 185                 190

Val Lys Gly Gly Asp Arg Ile Pro Ala Asp Leu Arg Ile Ile Ser Ala
        195                 200                 205
```

-continued

```
Asn Gly Cys Lys Val Asp Asn Ser Ser Leu Thr Gly Glu Ser Glu Pro
    210                 215                 220
Gln Thr Arg Ser Pro Asp Phe Thr Asn Glu Asn Pro Leu Glu Thr Arg
225                 230                 235                 240
Asn Ile Ala Phe Phe Ser Thr Asn Cys Val Glu Gly Thr Ala Arg Gly
                245                 250                 255
Ile Val Val Tyr Thr Gly Asp Arg Thr Val Met Gly Arg Ile Ala Thr
            260                 265                 270
Leu Ala Ser Gly Leu Glu Gly Gly Gln Thr Pro Ile Ala Glu Glu Ile
        275                 280                 285
Glu His Phe Ile His Leu Ile Thr Gly Val Ala Val Phe Leu Gly Val
    290                 295                 300
Ser Phe Phe Ile Leu Ser Leu Ile Leu Glu Tyr Thr Trp Leu Glu Ala
305                 310                 315                 320
Val Ile Phe Leu Ile Gly Ile Ile Val Ala Asn Val Pro Glu Gly Leu
                325                 330                 335
Leu Ala Thr Val Thr Val Cys Leu Thr Leu Thr Ala Lys Arg Met Ala
            340                 345                 350
Arg Lys Asn Cys Leu Val Lys Asn Leu Glu Ala Val Glu Thr Leu Gly
        355                 360                 365
Ser Thr Ser Thr Ile Cys Ser Asp Lys Thr Gly Thr Leu Thr Gln Asn
    370                 375                 380
Arg Met Thr Val Ala His Met Trp Phe Asp Asn Gln Ile His Glu Ala
385                 390                 395                 400
Asp Thr Thr Glu Asn Gln Ser Gly Val Ser Phe Asp Lys Thr Ser Ala
                405                 410                 415
Thr Trp Phe Ala Leu Ser Arg Ile Ala Gly Leu Cys Asn Arg Ala Val
            420                 425                 430
Phe Gln Ala Asn Gln Glu Asn Leu Pro Ile Leu Lys Arg Ala Val Ala
        435                 440                 445
Gly Asp Ala Ser Glu Ser Ala Leu Leu Lys Cys Ile Glu Val Cys Cys
    450                 455                 460
Gly Ser Val Met Glu Met Arg Glu Lys Tyr Thr Lys Ile Val Glu Ile
465                 470                 475                 480
Pro Phe Asn Ser Thr Asn Lys Tyr Gln Leu Ser Ile His Lys Asn Pro
                485                 490                 495
Asn Ala Ser Glu Pro Lys His Leu Leu Val Met Lys Gly Ala Pro Glu
            500                 505                 510
Arg Ile Leu Asp Arg Cys Ser Ser Ile Leu Leu His Gly Lys Glu Gln
        515                 520                 525
Pro Leu Asp Glu Glu Leu Lys Asp Ala Phe Gln Asn Ala Tyr Leu Glu
    530                 535                 540
Leu Gly Gly Leu Gly Glu Arg Val Leu Gly Phe Cys His Leu Leu Leu
545                 550                 555                 560
Pro Asp Glu Gln Phe Pro Glu Gly Phe Gln Phe Asp Thr Asp Glu Val
                565                 570                 575
Asn Phe Pro Val Asp Asn Leu Cys Phe Val Gly Leu Ile Ser Met Ile
            580                 585                 590
Asp Pro Pro Arg Ala Ala Val Pro Asp Ala Val Gly Lys Cys Arg Ser
        595                 600                 605
Ala Gly Ile Lys Val Ile Met Val Thr Gly Asp His Pro Ile Thr Ala
    610                 615                 620
```

-continued

```
Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Asn Gln Val Asn
                645                 650                 655

Pro Arg Asp Ala Lys Ala Cys Val Val His Gly Ser Asp Leu Lys Asp
            660                 665                 670

Met Thr Ser Glu Glu Leu Asp Asp Ile Leu Arg Tyr His Thr Glu Ile
        675                 680                 685

Val Phe Ala Arg Thr Ser Pro Gln Gln Lys Leu Ile Ile Val Glu Gly
    690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Val Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Phe His Leu Leu Gly Ile Arg Glu Thr Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Ala
                965                 970                 975

Ala Leu Arg Met Tyr Pro Leu Lys Pro Thr Trp Trp Phe Cys Ala Phe
            980                 985                 990

Pro Tyr Ser Leu Leu Ile Phe Val Tyr Asp Glu Val Arg Lys Leu Ile
        995                 1000                1005

Ile Arg Arg Arg Pro Gly Gly Trp Val Glu Lys Glu Thr Tyr Tyr
    1010                1015                1020
```

<210> SEQ ID NO 3
<211> LENGTH: 3636
<212> TYPE: DNA

```
<213> ORGANISM: Rattus norvegicus
<220> FEATURE:
<221> NAME/KEY: CDS
<222> LOCATION: (238)...(3309)

<400> SEQUENCE: 3
```

| | | |
|---|---|---|
| ggagcctcgg cgggaggagg cggacacgtg gcagcggcgg cggcagcggc agcagcagcg | 60 | |
| gcggcagcag cggcggcctc ggtccggggc gccggccgtc ctccctcttt cctccggcgg | 120 | |
| cagccctagt tcccgcctct cggctccccc ggctccactc tcccagccgg gagctgctct | 180 | |
| ctcctctttc tagtctccag ccacaggacc cggcgcgggg cccgcagcgc cgccacc atg<br>                                                                                                                       Met<br>                                                                                                                       1 | 240 | |

```
ggg aag ggg gtt gga cga gac aag tat gag ccc gca gct gta tca gaa       288
Gly Lys Gly Val Gly Arg Asp Lys Tyr Glu Pro Ala Ala Val Ser Glu
            5                  10                  15 cat ggg gac aag aag agc aag aag gcg aag aag gaa agg gac atg gac       336
His Gly Asp Lys Lys Ser Lys Lys Ala Lys Lys Glu Arg Asp Met Asp
         20                  25                  30 gaa ctc aag aag gaa gtg tct atg gac gac cat aaa ctc agc ctg gat       384
Glu Leu Lys Lys Glu Val Ser Met Asp Asp His Lys Leu Ser Leu Asp
 35                  40                  45 gaa ctc cat cgt aaa tac gga aca gat ttg agc cga ggc cta aca ccc       432
Glu Leu His Arg Lys Tyr Gly Thr Asp Leu Ser Arg Gly Leu Thr Pro
 50                  55                  60                  65 gca agg gcc gct gag atc ctg gct cgg gat ggc ccc aac gcc ctc acg       480
Ala Arg Ala Ala Glu Ile Leu Ala Arg Asp Gly Pro Asn Ala Leu Thr
                 70                  75                  80 ccc cct ccc act act ccc gag tgg gtc aaa ttc tgt cgg cag ctg ttc       528
Pro Pro Pro Thr Thr Pro Glu Trp Val Lys Phe Cys Arg Gln Leu Phe
             85                  90                  95 ggt ggc ttc tcc atg tta ctg tgg att gga gcc att ctt tgt ttc ttg       576
Gly Gly Phe Ser Met Leu Leu Trp Ile Gly Ala Ile Leu Cys Phe Leu
        100                 105                 110 gct tat ggc atc cga agt gct aca gaa gag gaa cca cca aat gat gat       624
Ala Tyr Gly Ile Arg Ser Ala Thr Glu Glu Glu Pro Pro Asn Asp Asp
    115                 120                 125 ctg tac ctc ggg gtc gtg ctg tct gct gtc gtc atc ata act ggc tgt       672
Leu Tyr Leu Gly Val Val Leu Ser Ala Val Val Ile Ile Thr Gly Cys
130                 135                 140                 145 ttc tcc tat tat caa gaa gca aaa agc tcc aag atc atg gaa tcc ttc       720
Phe Ser Tyr Tyr Gln Glu Ala Lys Ser Ser Lys Ile Met Glu Ser Phe
                150                 155                 160 aag aac atg gtc cct cag caa gcc ctc gtg att cga aat gga gag aag       768
Lys Asn Met Val Pro Gln Gln Ala Leu Val Ile Arg Asn Gly Glu Lys
            165                 170                 175 atg agc atc aac gca gag gat gtc gtc gtt ggt gat ctg gtg gag gtg       816
Met Ser Ile Asn Ala Glu Asp Val Val Val Gly Asp Leu Val Glu Val
        180                 185                 190 aag ggc gga gac cga atc cct gct gat ctc aga atc ata tct gca aat       864
Lys Gly Gly Asp Arg Ile Pro Ala Asp Leu Arg Ile Ile Ser Ala Asn
    195                 200                 205 ggc tgc aag gtg gat aac tcc tca ctc act ggt gaa tca gaa ccc cag       912
Gly Cys Lys Val Asp Asn Ser Ser Leu Thr Gly Glu Ser Glu Pro Gln
210                 215                 220                 225 act cgg tcc ccg gat ttc aca aac gag aac ccc ttg gag aca agg aac       960
Thr Arg Ser Pro Asp Phe Thr Asn Glu Asn Pro Leu Glu Thr Arg Asn
                230                 235                 240 att gcc ttc ttc tca acc aac tgt gtt gaa gga act gca cgt ggc atc     1008
Ile Ala Phe Phe Ser Thr Asn Cys Val Glu Gly Thr Ala Arg Gly Ile
```

|     |     |     |     |     |     |     |     |     |     |     |     |     |     |     |     |      |
|---|---|---|---|---|---|---|---|---|---|---|---|---|---|---|---|---|
|     |     |     | 245 |     |     |     |     | 250 |     |     |     |     | 255 |     |     |      |
| gtt | gtg | tac | act | ggg | gat | cgc | acc | gtg | atg | ggc | agg | atc | gcc | acc | ctt | 1056 |
| Val | Val | Tyr | Thr | Gly | Asp | Arg | Thr | Val | Met | Gly | Arg | Ile | Ala | Thr | Leu |      |
|     |     | 260 |     |     |     |     | 265 |     |     |     |     | 270 |     |     |     |      |
| gct | tct | ggg | ctg | gaa | ggc | ggc | ctg | acc | ccc | att | gct | gaa | gaa | atc | gag | 1104 |
| Ala | Ser | Gly | Leu | Glu | Gly | Gly | Leu | Thr | Pro | Ile | Ala | Glu | Glu | Ile | Glu |      |
|     | 275 |     |     |     |     | 280 |     |     |     |     | 285 |     |     |     |     |      |
| cac | ttc | atc | cac | ctc | atc | acg | ggt | gtg | gcc | gtg | ttc | ctg | ggg | gtg | tct | 1152 |
| His | Phe | Ile | His | Leu | Ile | Thr | Gly | Val | Ala | Val | Phe | Leu | Gly | Val | Ser |      |
| 290 |     |     |     |     | 295 |     |     |     |     | 300 |     |     |     |     | 305 |      |
| ttc | ttc | att | ctc | tct | ctg | atc | ctt | gag | tac | acc | tgg | ctc | gag | gct | gtc | 1200 |
| Phe | Phe | Ile | Leu | Ser | Leu | Ile | Leu | Glu | Tyr | Thr | Trp | Leu | Glu | Ala | Val |      |
|     |     |     |     | 310 |     |     |     |     | 315 |     |     |     |     | 320 |     |      |
| atc | ttc | ctc | att | ggt | atc | atc | gta | gcc | aac | gtg | ccg | gaa | ggt | ttg | ctg | 1248 |
| Ile | Phe | Leu | Ile | Gly | Ile | Ile | Val | Ala | Asn | Val | Pro | Glu | Gly | Leu | Leu |      |
|     |     |     | 325 |     |     |     |     | 330 |     |     |     |     | 335 |     |     |      |
| gcc | acc | gtc | acg | gta | tgt | ctg | acg | ctc | act | gcc | aag | cgc | atg | gcg | agg | 1296 |
| Ala | Thr | Val | Thr | Val | Cys | Leu | Thr | Leu | Thr | Ala | Lys | Arg | Met | Ala | Arg |      |
|     |     | 340 |     |     |     |     | 345 |     |     |     |     | 350 |     |     |     |      |
| aag | aac | tgc | ctg | gtg | aag | aac | ctg | gaa | gct | gtg | gag | acc | ttg | ggg | tcc | 1344 |
| Lys | Asn | Cys | Leu | Val | Lys | Asn | Leu | Glu | Ala | Val | Glu | Thr | Leu | Gly | Ser |      |
|     | 355 |     |     |     |     | 360 |     |     |     |     | 365 |     |     |     |     |      |
| aca | tcc | acc | atc | tgc | tcc | gac | aag | act | gga | act | ctg | act | cag | aac | cgg | 1392 |
| Thr | Ser | Thr | Ile | Cys | Ser | Asp | Lys | Thr | Gly | Thr | Leu | Thr | Gln | Asn | Arg |      |
| 370 |     |     |     |     | 375 |     |     |     |     | 380 |     |     |     |     | 385 |      |
| atg | aca | gtg | gct | cac | atg | tgg | ttt | gac | aat | caa | atc | cat | gaa | gct | gac | 1440 |
| Met | Thr | Val | Ala | His | Met | Trp | Phe | Asp | Asn | Gln | Ile | His | Glu | Ala | Asp |      |
|     |     |     |     | 390 |     |     |     |     | 395 |     |     |     |     | 400 |     |      |
| acc | aca | gag | aat | cag | agt | ggg | gtc | tcc | ttt | gac | aag | acg | tca | gcc | acc | 1488 |
| Thr | Thr | Glu | Asn | Gln | Ser | Gly | Val | Ser | Phe | Asp | Lys | Thr | Ser | Ala | Thr |      |
|     |     |     | 405 |     |     |     |     | 410 |     |     |     |     | 415 |     |     |      |
| tgg | ttc | gct | ctg | tcc | aga | att | gct | ggt | ctc | tgt | aac | agg | gca | gtg | ttt | 1536 |
| Trp | Phe | Ala | Leu | Ser | Arg | Ile | Ala | Gly | Leu | Cys | Asn | Arg | Ala | Val | Phe |      |
|     |     | 420 |     |     |     |     | 425 |     |     |     |     | 430 |     |     |     |      |
| cag | gct | aac | caa | gaa | aac | ctg | cct | atc | ctt | aag | cgt | gca | gta | gcg | gga | 1584 |
| Gln | Ala | Asn | Gln | Glu | Asn | Leu | Pro | Ile | Leu | Lys | Arg | Ala | Val | Ala | Gly |      |
|     | 435 |     |     |     |     | 440 |     |     |     |     | 445 |     |     |     |     |      |
| gat | gct | tcc | gag | tcg | gcg | ctc | tta | aag | tgc | atc | gag | gtc | tgc | tgt | ggc | 1632 |
| Asp | Ala | Ser | Glu | Ser | Ala | Leu | Leu | Lys | Cys | Ile | Glu | Val | Cys | Cys | Gly |      |
| 450 |     |     |     |     | 455 |     |     |     |     | 460 |     |     |     |     | 465 |      |
| tcc | gtg | atg | gag | atg | agg | gag | aag | tac | acc | aag | ata | gtg | gag | att | ccc | 1680 |
| Ser | Val | Met | Glu | Met | Arg | Glu | Lys | Tyr | Thr | Lys | Ile | Val | Glu | Ile | Pro |      |
|     |     |     |     | 470 |     |     |     |     | 475 |     |     |     |     | 480 |     |      |
| ttc | aac | tcc | acc | aac | aag | tac | cag | ctc | tcc | att | cac | aag | aac | cca | aac | 1728 |
| Phe | Asn | Ser | Thr | Asn | Lys | Tyr | Gln | Leu | Ser | Ile | His | Lys | Asn | Pro | Asn |      |
|     |     |     | 485 |     |     |     |     | 490 |     |     |     |     | 495 |     |     |      |
| gca | tcg | gag | cct | aag | cac | ctg | cta | gtg | atg | aag | ggc | gcc | cca | gaa | agg | 1776 |
| Ala | Ser | Glu | Pro | Lys | His | Leu | Leu | Val | Met | Lys | Gly | Ala | Pro | Glu | Arg |      |
|     |     | 500 |     |     |     |     | 505 |     |     |     |     | 510 |     |     |     |      |
| atc | ctg | gac | cga | tgc | agt | tct | atc | ctc | ctc | cac | ggc | aag | gag | cag | ccc | 1824 |
| Ile | Leu | Asp | Arg | Cys | Ser | Ser | Ile | Leu | Leu | His | Gly | Lys | Glu | Gln | Pro |      |
|     | 515 |     |     |     |     | 520 |     |     |     |     | 525 |     |     |     |     |      |
| ctg | gac | gaa | gag | ctg | aag | gac | gcc | ttt | cag | aat | gcc | tac | cta | gag | ctg | 1872 |
| Leu | Asp | Glu | Glu | Leu | Lys | Asp | Ala | Phe | Gln | Asn | Ala | Tyr | Leu | Glu | Leu |      |
| 530 |     |     |     |     | 535 |     |     |     |     | 540 |     |     |     |     | 545 |      |
| ggg | ggc | ctt | gga | gag | cgt | gtg | cta | ggt | ttc | tgc | cac | ctc | ctt | ctg | cct | 1920 |
| Gly | Gly | Leu | Gly | Glu | Arg | Val | Leu | Gly | Phe | Cys | His | Leu | Leu | Leu | Pro |      |
|     |     |     |     | 550 |     |     |     |     | 555 |     |     |     |     | 560 |     |      |
| gac | gaa | cag | ttt | ccc | gaa | ggc | ttc | cag | ttt | gac | act | gat | gaa | gtc | aat | 1968 |

-continued

```
Asp Glu Gln Phe Pro Glu Gly Phe Gln Phe Asp Thr Asp Glu Val Asn
            565                 570                 575 ttc ccc gtg gat aac ctc tgc ttc gtg ggt ctt atc tcc atg att gac      2016
Phe Pro Val Asp Asn Leu Cys Phe Val Gly Leu Ile Ser Met Ile Asp
        580                 585                 590 cct cct cga gct gct gtc ccc gat gct gtg ggc aaa tgc cgc agc gct      2064
Pro Pro Arg Ala Ala Val Pro Asp Ala Val Gly Lys Cys Arg Ser Ala
595                 600                 605 ggg att aag gtc atc atg gtc aca gga gac cat cca atc aca gcc aaa      2112
Gly Ile Lys Val Ile Met Val Thr Gly Asp His Pro Ile Thr Ala Lys
610                 615                 620                 625 gcc att gct aag ggg gtg ggc att atc tca gaa ggt aac gag acc gtg      2160
Ala Ile Ala Lys Gly Val Gly Ile Ile Ser Glu Gly Asn Glu Thr Val
            630                 635                 640 gaa gac att gct gcc cgc ctc aac att cca gtg aac cag gtg aac ccc      2208
Glu Asp Ile Ala Ala Arg Leu Asn Ile Pro Val Asn Gln Val Asn Pro
        645                 650                 655 aga gat gcc aag gcc tgt gta gta cat ggc agt gac ttg aag gac atg      2256
Arg Asp Ala Lys Ala Cys Val Val His Gly Ser Asp Leu Lys Asp Met
660                 665                 670 acc tct gag gag ctg gat gac att ttg cgg tac cac acg gag att gtc      2304
Thr Ser Glu Glu Leu Asp Asp Ile Leu Arg Tyr His Thr Glu Ile Val
675                 680                 685 ttt gct agg acc tct cct caa cag aag ctc atc att gtg gag ggc tgc      2352
Phe Ala Arg Thr Ser Pro Gln Gln Lys Leu Ile Ile Val Glu Gly Cys
690                 695                 700                 705 cag cgg cag ggt gcc atc gtg gct gtc aca ggg gat ggt gtc aat gac      2400
Gln Arg Gln Gly Ala Ile Val Ala Val Thr Gly Asp Gly Val Asn Asp
                710                 715                 720 tct cca gct ttg aaa aag gca gat att ggg gtt gcc atg ggg att gtt      2448
Ser Pro Ala Leu Lys Lys Ala Asp Ile Gly Val Ala Met Gly Ile Val
            725                 730                 735 ggc tcg gat gtg tcc aag caa gct gct gac atg att ctt ctg gat gac      2496
Gly Ser Asp Val Ser Lys Gln Ala Ala Asp Met Ile Leu Leu Asp Asp
        740                 745                 750 aac ttt gcc tcc atc gtg act gga gta gaa gaa ggt cgt ctg ata ttt      2544
Asn Phe Ala Ser Ile Val Thr Gly Val Glu Glu Gly Arg Leu Ile Phe
755                 760                 765 gat aac ttg aag aaa tcc att gct tac acc cta aca agt aac att ccg      2592
Asp Asn Leu Lys Lys Ser Ile Ala Tyr Thr Leu Thr Ser Asn Ile Pro
770                 775                 780                 785 gaa atc acc ccc ttc ttg ata ttt att att gca aac att cca ctg ccc      2640
Glu Ile Thr Pro Phe Leu Ile Phe Ile Ile Ala Asn Ile Pro Leu Pro
                790                 795                 800 ctg ggc acc gtg acc atc ctc tgc att gac ttg ggc act gac atg gtt      2688
Leu Gly Thr Val Thr Ile Leu Cys Ile Asp Leu Gly Thr Asp Met Val
            805                 810                 815 ccc gcc atc tct ctg gcc tat gaa cag gct gaa agt gac atc atg aag      2736
Pro Ala Ile Ser Leu Ala Tyr Glu Gln Ala Glu Ser Asp Ile Met Lys
        820                 825                 830 agg cag ccc aga aat ccc aaa acg gac aaa ctt gtg aac gag cgt ctg      2784
Arg Gln Pro Arg Asn Pro Lys Thr Asp Lys Leu Val Asn Glu Arg Leu
835                 840                 845 atc agc atg gcc tat gga cag atc ggt atg atc cag gcc ctg gga ggc      2832
Ile Ser Met Ala Tyr Gly Gln Ile Gly Met Ile Gln Ala Leu Gly Gly
850                 855                 860                 865 ttc ttc act tat ttt gtg att ctg gct gag aac ggt ttc ctg ccc ttt      2880
Phe Phe Thr Tyr Phe Val Ile Leu Ala Glu Asn Gly Phe Leu Pro Phe
                870                 875                 880
```

```
cac ctg ttg ggc atc cga gag acc tgg gat gac cgc tgg att aat gat    2928
His Leu Leu Gly Ile Arg Glu Thr Trp Asp Asp Arg Trp Ile Asn Asp
            885                 890                 895 gtg gag gac agc tac ggg cag cag tgg acc tac gag cag agg aag att    2976
Val Glu Asp Ser Tyr Gly Gln Gln Trp Thr Tyr Glu Gln Arg Lys Ile
        900                 905                 910 gtg gag ttc acc tgc cac acg gcc ttc ttt gtc agt atc gtg gta gtg    3024
Val Glu Phe Thr Cys His Thr Ala Phe Phe Val Ser Ile Val Val Val
    915                 920                 925 cag tgg gct gac ttg gtc atc tgc aag acc aga agg aat tct gtc ttc    3072
Gln Trp Ala Asp Leu Val Ile Cys Lys Thr Arg Arg Asn Ser Val Phe
930                 935                 940                 945 cag cag gga atg aag aac aag atc tta ata ttt ggc ctc ttt gaa gag    3120
Gln Gln Gly Met Lys Asn Lys Ile Leu Ile Phe Gly Leu Phe Glu Glu
                950                 955                 960 aca gct ctt gct gct ttc ctg tcc tac tgc cct ggg atg ggt gca gcc    3168
Thr Ala Leu Ala Ala Phe Leu Ser Tyr Cys Pro Gly Met Gly Ala Ala
            965                 970                 975 ctt agg atg tat ccc ctc aaa cct act tgg tgg ttc tgt gcc ttc ccc    3216
Leu Arg Met Tyr Pro Leu Lys Pro Thr Trp Trp Phe Cys Ala Phe Pro
        980                 985                 990 tac tcc ctt ctc atc ttc gtg tat gac gag gtg cgg aag ctc atc atc    3264
Tyr Ser Leu Leu Ile Phe Val Tyr Asp Glu Val Arg Lys Leu Ile Ile
    995                 1000                1005 agg cga cgc cct ggc ggc tgg gtg gag aag gaa acc tac tac tag        3309
Arg Arg Arg Pro Gly Gly Trp Val Glu Lys Glu Thr Tyr Tyr *
1010                1015                1020 cccactgccc tgcacgccgt ggaacattgt gccacacact gcacctaccc ctaccccccc    3369
tttgtgtact tcaagtcttg gagctcggaa ctctaccctg gtaggaaagc accaaagcat    3429
gtggggatcc agacgtcctg gaatgaagca tgtagctgta atgggggcg gggggagggc    3489 tgcccgaaaa acaccgtgga cggggacgac agcggggaag gtttatatgt gcctttttgt    3549
ttttgtaaaa aaggaaaaacc tggaaagact gaaagattac gttttatatc tggattttta    3609
caaataaaga tggctattat aacggaa                                       3636
```

<210> SEQ ID NO 4
<211> LENGTH: 1023
<212> TYPE: PRT
<213> ORGANISM: Rattus norvegicus

<400> SEQUENCE: 4

```
Met Gly Lys Gly Val Gly Arg Asp Lys Tyr Glu Pro Ala Ala Val Ser
1               5                   10                  15

Glu His Gly Asp Lys Lys Ser Lys Ala Lys Lys Glu Arg Asp Met
            20                  25                  30

Asp Glu Leu Lys Lys Glu Val Ser Met Asp Asp His Lys Leu Ser Leu
        35                  40                  45

Asp Glu Leu His Arg Lys Tyr Gly Thr Asp Leu Ser Arg Gly Leu Thr
    50                  55                  60

Pro Ala Arg Ala Ala Glu Ile Leu Ala Arg Asp Gly Pro Asn Ala Leu
65                  70                  75                  80

Thr Pro Pro Pro Thr Thr Pro Glu Trp Val Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Gly Ile Arg Ser Ala Thr Glu Glu Glu Pro Pro Asn Asp
        115                 120                 125
```

```
Asp Leu Tyr Leu Gly Val Val Leu Ser Ala Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Asp Val Val Gly Asp Leu Val Glu
            180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Leu Thr Pro Ile Ala Glu Glu Ile
        275                 280                 285

Glu His Phe Ile His Leu Ile Thr Gly Val Ala Val Phe Leu Gly Val
    290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
    370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Phe Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
        435                 440                 445

Gly Asp Ala Ser Glu Ser Ala Leu Leu Lys Cys Ile Glu Val Cys Cys
    450                 455                 460

Gly Ser Val Met Glu Met Arg Glu Lys Tyr Thr Lys Ile Val Glu Ile
465                 470                 475                 480

Pro Phe Asn Ser Thr Asn Lys Tyr Gln Leu Ser Ile His Lys Asn Pro
                485                 490                 495

Asn Ala Ser Glu Pro Lys His Leu Leu Val Met Lys Gly Ala Pro Glu
            500                 505                 510

Arg Ile Leu Asp Arg Cys Ser Ser Ile Leu Leu His Gly Lys Glu Gln
        515                 520                 525

Pro Leu Asp Glu Glu Leu Lys Asp Ala Phe Gln Asn Ala Tyr Leu Glu
    530                 535                 540
```

-continued

```
Leu Gly Gly Leu Gly Glu Arg Val Leu Gly Phe Cys His Leu Leu Leu
545                 550                 555                 560

Pro Asp Glu Gln Phe Pro Glu Gly Phe Gln Phe Asp Thr Asp Glu Val
                565                 570                 575

Asn Phe Pro Val Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
        595                 600                 605

Ala Gly Ile Lys Val Ile Met Val Thr Gly Asp His Pro Ile Thr Ala
    610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Asn Gln Val Asn
                645                 650                 655

Pro Arg Asp Ala Lys Ala Cys Val Val His Gly Ser Asp Leu Lys Asp
            660                 665                 670

Met Thr Ser Glu Glu Leu Asp Asp Ile Leu Arg Tyr His Thr Glu Ile
        675                 680                 685

Val Phe Ala Arg Thr Ser Pro Gln Gln Lys Leu Ile Ile Val Glu Gly
    690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Val Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Phe His Leu Leu Gly Ile Arg Glu Thr Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Ala
```

-continued

```
                    965                 970                 975
Ala Leu Arg Met Tyr Pro Leu Lys Pro Thr Trp Trp Phe Cys Ala Phe
            980                 985                 990

Pro Tyr Ser Leu Leu Ile Phe Val Tyr Asp Glu Val Arg Lys Leu Ile
        995                 1000                1005

Ile Arg Arg Arg Pro Gly Gly Trp Val Glu Lys Glu Thr Tyr Tyr
    1010                1015                1020
```

METHOD OF ASSAYING MODULATORS OF HYPERTENSION

CROSS REFERENCE TO RELATED APPLICATIONS

This application is a continuation application and claims priority from Utility application Ser. No. 09/653,030, filed Sep. 1, 2000, now abandoned, which claims priority from Provisional Application 60/152,011, filed Sep. 1, 1999.

STATEMENT AS TO FEDERALLY SPONSORED RESEARCH

The invention was made with funding from the National Institutes of Health, grants HL 58136 and HL 48903. The government may have certain rights in the invention.

FIELD OF THE INVENTION

The invention relates to methods useful for delaying or ameliorating diseases associated with hypertension.

BACKGROUND OF THE INVENTION

Essential hypertension (EHT; 1) is a paradigmatic, complex; and multifactorial condition. Genes that mediate EHT have therefore been difficult to isolate and characterize, requiring multiple lines of evidence to establish their roles in EHT pathogenesis.

In view of the wide range of disorders that are associated with hypertension, it would be desirable to identify compounds for the treatment or prevention of hypertension.

SUMMARY OF THE INVENTION

Here we present evidence of the identification and characterization of an EHT susceptibility gene. The invention provides methods for identifying compounds which affect hypertension.

In one aspect, the invention features a method of assaying a test compound, by providing a non-human mammal with a functionally variant hypertension susceptibility gene, administering said test compound to said non-human mammal, and determining whether the test compound affects hypertension parameters in the non-human mammal relative to a non-human mammal containing a wild type hypertension susceptibility gene.

In preferred embodiments of the invention, the hypertension susceptibility gene is the $\alpha 1$ Na,K ATPase gene and the non-human mammal is a rat, preferably the Dahl S rat.

By "test compound" is meant any chemical compound, be it naturally-occurring or artificially-derived. Test compounds may include, for example, peptides, polypeptides, synthesized organic molecules, naturally occurring organic molecules, and nucleic acid molecules.

By "affects" is meant changes, either by increase or decrease.

By "determining" is meant analyzing the effect of a test compound on the test system. The readout of the analysis may be measurement of life span, blood pressure, renal pathology, and other hypertension parameters known to those skilled in the art.

The invention provides a means for assaying compounds that affect hypertension by means of an animal model in which a hypertension susceptibility gene has been identified. Other features and advantages of the invention will be apparent from the following detailed description, and from the claims.

BRIEF DESCRIPTION OF THE DRAWINGS

FIGS. 4A–4G show the comparative analysis of degree of hypertensive renal disease.

DETAILED DESCRIPTION OF THE INVENTION

Figure 1A:
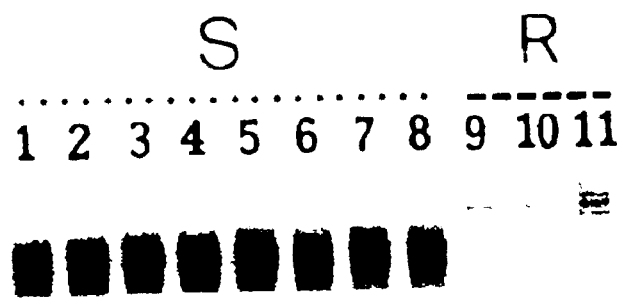
FIGS. 1A–1B show the genetic analysis of Dahl $S^{HSD\ rats}$.

Given the difficulty of isolation and characterization of genes mediating EHT, delineation of a putative EHT susceptibility gene should meet the following criteria: 1, identification of a functionally significant structural mutation in the relevant gene; 2, concordance of the observed genetic dysfunction with a pathophysiologic mechanism logical to the hypertension pathogenesis; 3, association of the putative hypertension susceptibility gene with hypertension in validated genetic animal models or human hypertensive patients; and 4, delineation of the mechanistic role in an in vivo model (1, 2). To date, no EHT susceptibility gene has been identified that meets all these criteria.

To simplify the molecular genetic characterization of an EHT susceptibility gene, one subtype of EHT, salt-sensitive hypertension (SS-EHT), was studied. The hypothesis that variants of the $\alpha 1$ Na,K-ATPase gene mediate SS-EHT in a genetic rat model of hypertension, was tested using the Dahl S hypertensive rat strain (3, 4). Because $\alpha 1$ Na,K-ATPase is the sole active Na+ transporter in the renal basolateral epithelia throughout the nephron (5, 6), it is a logical candidate gene to be considered in the assessment of the abnormal renal sodium handling in the Dahl S rat (7).

Two of the four criteria stated above (1, 2) and required to define the $\alpha 1$ Na,K-ATPase gene as an EHT susceptibility gene have been met. For criterion 1, a Q276L substitution in the $\alpha 1$ Na,K-ATPase gene in inbred Dahl S rats from Harlan Sprague Dawley, Inc. (Indianapolis, Ind.) (Dahl SHSD) has been characterized (8, 9). In contrast to the non-detection by PCR sequencing reported by Simonet et al. (10), the Q276L $\alpha 1$ Na,K-ATPase variant was confirmed in Dahl S genomic DNA by using PCR error-independent assays (polymerase allele specific amplification, PASA, and 3' mismatch correction assay) and ligase chain reaction assay; in kidney RNA by $RT^{th}$-PCR; and in cDNA clones by resequencing (9). Likewise, detection of the wild-type (wt) Q276 sequence (11) was confirmed in Dahl R genomic DNA and in resequenced cDNA clones (9).

The Q276L mutation results in decreased K+($^{86}$Rβ+) influx detected in *Xenopus* oocyte expression experiments using both Dahl S kidney polyA+ RNA, as well as in vitro transcribed variant Q276L-specific cRNA transcript, in contrast to control Dahl R rat kidney polyA+ RNA and in vitro transcribed wt Q276 cRNA transcript, respectively (8). Kinetic studies of $\alpha 1$ Na,K-ATPases in red blood cell flux experiments, comparing Dahl S and Dahl R $\alpha 1$ Na,K-ATPases corroborated decreased K+($^{86}$Rβ+) influx and revealed normal Na+ transport resulting in an increased Na:K coupling ratio in the Dahl S Q276L $\alpha 1$ Na,K-ATPase variant (12). For criterion 2, simulated modeling studies have revealed that consequences of an increased Na:K coupling ratio (from 3:2 to 3:1) observed in the Q276L $\alpha 1$ Na,K-ATPase variant results in an altered set point for cellular Na+ metabolism, with higher sodium reabsorption at unchanged Na,K-ATPase levels in the proximal convoluted tubule, as well as in the thick ascending limb of the loop of Henle (13), thus providing a mechanistic hypothesis for increased Na+ reabsorption in Dahl S rats.

To fulfill criteria 3 and 4, the following questions were addressed: does the Q276L α1 Na,K-ATPase variant contribute to the salt-sensitive hypertension phenotype? and does the functionally aberrant Q276L α1 Na,K-ATPase allele cosegregate with salt-sensitive hypertension? These questions were addressed using transgenic experiments and a standard intercross linkage analysis strategy.

Because of the inadvertent genetic contamination of the Dahl $S^{HSD}$ strain (19, 24), transgenic studies were performed using only Dahl $S^{HSD}$ rats from the foundation colonies at Harlan Sprague, Inc. confirmed as to genotype and salt-sensitive phenotype (19). The F2 intercross was also done using Dahl $S^{HSD}$ and Dahl $R^{HSD}$ rats confirmed for both genotype and phenotype. Unequivocal observations are thus ascertained (19).

The results obtained from the transgenic and cosegregation studies fulfill the requirements of the criteria set out to definitively assign the α1 Na,K-ATPase gene as a susceptibility gene for hypertension using the Dahl SHSD genetic hypertension rat model. The concordance of improvement not just in all measures of blood pressure, but also in renal disease and life span, provides holistic support strengthening the ascertainment of the mechanistic role of α1 Na,K-ATPase in salt-sensitive hypertension as modeled in the Dahl $S^{HSD}$ rat. The results indicate that phenotypic differences observed in the transgenic Tg[wtα1] rats are most likely due to the functional heterozygosity of wt and Q276L variant α1 Na,K-ATPases rather than an additive overabundance of α1 Na,K-ATPases. This is consistent with the observation made from blood pressure data of F1(S×R) rats, indicating that hypertension is a recessive trait and that normotension is a dominant trait.

Other genetic studies have documented previous linkage of the α1 Na,K-ATPase locus. The α1 Na,K-ATPase locus was found to be the closest candidate gene in a total chromosome 2 scan analyzing two F2 cohorts, one involving the Dahl S×Milan normotensive strain, and one involving Dahl S×Wistar Kyoto normotensive strain (22). Recent studies on chromosome 2 analyzing F2 crosses derived from the stroke-prone spontaneously hypertensive rat and the normotensive Wistar-Kyoto rat (25) and derived from the spontaneously hypertensive rat and the Wistar-Kyoto rat (26) have also detected a QTL for high blood pressure close to the α1 Na,K-ATPase locus. The cosegregation study presented herein independently confirms these previous results and with P<0.003, meets the required nominal P<0.01 criterion for confirmed linkage (27).

The pronounced improvement in blood pressure (~40%) by the transgenic manipulation of a single gene suggests that hypertension, being polygenic, does not, most likely, follow a simple additive model of genetic inheritance, but rather involves a di- or multigenic interaction within a polygenic context. With normotension being dominant, transgenic experiments designed to correct hypertension in the inbred hypertensive strain would be more robust in investigating the effects of interacting hypertension susceptibility genes rather than F2 intercross studies with polymorphic markers as shown herein.

The improvement of multiple pathogenic events in transgenic Tg[wtα1] Dahl S rats is consistent with observations in human hypertensive patients, wherein lowering of blood pressure has been shown to decrease mortality and target organ complications (28). The greater reduction in the degree of renal pathology (50%) and greater improvement in life span (75.6%) compared with blood pressure parameters (~40%) seen in the transgenic rats could be attributed to an "early" intervention, as the transgenic rats have the corrective transgene from one-cell embryo stage—a finding which promotes the value of early preventive interventions for some complex diseases. Additionally, the α1 Na,K-ATPase gene might play a role in hypertensive renal complication pathogenesis that is distinct from its role in hypertension pathogenesis, and/or a threshold phenomenon might be involved in the pathogenesis of hypertensive target organ complications.

The inability to detect the $A^{1079}$–$T^{1079}$ transversion in Dahl S rat genomic DNA via amplification-based methods and sequencing of genomic clones underscores the importance of a multifaceted analysis of such refractory mutations encompassing structural and functional approaches. The demonstration, therefore, of functionally significant differences between Dahl S and Dahl R α1 Na,K-ATPases and, more significantly, the partial correction of salt-sensitive hypertension in the Dahl S rat via transgenesis support the contention that the Q276L mutation exists in Dahl S rats as shown by error-independent assays and that it plays a role in salt-sensitive hypertension. The observation of an amplification error-prone genomic DNA region raises the question that other mutations might be similarly refractory to detection by conventional amplification-based methods. Amplification-independent assays provide an alternative and suitable approach to structurally assess these "refractory" mutations.

Altogether, the results presented herein demonstrate that the Na,K-ATPase locus is a SS-EHT susceptibility gene and showcases the strength of a "forward genetics approach" testing functionally significant variant alleles at biologically relevant loci (1, 29)—as was done recently in the study of the variant the value of a multifaceted molecular genetic approach (1, 31), wherein transgenic rat experiments in an inbred model organism might allow one to deduce the role of a gene in complex disease pathogenesis. The success in the significant alleviation of salt-sensitive hypertension by the manipulation of a single gene validates the potential for gene therapy for complex cardiovascular diseases and other multifactorial disorders. Moreover, the proposed criteria and approach in animal models provide evidence that make analogous studies of homologous human genes in hypertension compelling.

The following examples are to illustrate the invention. They are not meant to limit the invention in any way.

EXAMPLE 1

Methods

Genotype and PASA Analysis of Dahl S and Dahl R Rats.

Foundation colony Dahl S and Dahl R rats were obtained from Harlan Sprague Dawley Inc. derived from breeding pairs procured from J. Rapp (Medical College of Ohio, Toledo, Ohio) in 1985. Newly obtained Dahl $S^{Rapp}$ rats from J. Rapp were obtained by and analyzed by Harlan Sprague Dawley, Inc. (Indianapolis, Ind.) for comparative analysis. All marker rat map pairs were obtained from Research Genetics (Huntsville, Ala.). Genotyping conditions were optimized and done as described (9, 14). For PASA analysis, rat spleen genomic DNA was isolated and PASA was done using primer pairs and conditions essentially as described (9) with the following modifications: the optimal stringent PCR cycling conditions were as follows: 95° C.×10 min; 30 cycles of (95° C.×1 min, 57° C.×1 min, 72° C.×1 min); extension at 72° C.×7 min with 0.5 U/10 μL of AmpliTaq Gold™ (Perkin Elmer Corp., Norwalk, Conn.).

Development of Dahl S Transgenic Rats.

The transgene was constructed linking the wt α1 Na,K-ATPase (1288)5' flanking region tested for functionality in tissue culture cells (15), full length 5' UT, full length 1028-amino acid-coding region, 131 bp of 3' UT of the wt α1 Na,K-ATPase cDNA, and 199 bp of SV40 polyadenylation signal sequences. Linearization with PvuI and HindIII restriction enzymes released the intact Tg[wtα1] minigene with 233 bp of vector sequence 5' to the minigene, and 237 bp of vector sequence 3' to the minigene, resulting in a total of 5,376 bp. Transgenic rats were developed as described (16) and three founders ($Tg_{24}$, $Tg_{37}$, and $Tg_{48}$) were identified by Southern blot analysis. Only two lines were bred to homozygosity: $Tg[wt\alpha 1]_{24}$ and $Tg[wt\alpha 1]_{48}$.

Ribonuclease Protection Assays (RPAs).

RPA was performed with the RPA I™ ribonuclease protection assay kit (Ambion, Austin, Tex.) as per manufacturer's instructions. The riboprobe was designed to span 131 bp of 3' untranslated region of the rat α1 Na,K-ATPase and 109 bp of SV40 sequence distinguishing the transgene transcript as a 240-nucleotide (nt) protected fragment in contrast to the 131-nt protected fragment of endogenous α1 Na,K-ATPase transcript. 20 μg of total cellular RNA purified by the guanidinium-CsCl method was used for each assay.

Isolation of Rat Kidney Rough Microsomes.

Membrane-bound polysomes were isolated as described (17) using a cation (CsCl)-containing sucrose gradient. The pelleted rough microsomes were dissolved in 10 mM Tris-HCL, pH 7.4, 1 mM EDTA, and the total rough microsomal RNA was isolated by sequential phenol:chloroform (50:50) extraction followed by ethanol precipitation. 20 μg of rat kidney membrane-bound polysomal RNA was used for RPA using the same riboprobe and experimental conditions described above.

Assessment of Life Span.

Life span was assessed in both hemizygous and homozygous transgenic rats. Hemizygous male and female transgenic rats from three lines, along with littermate non-transgenic controls were started on a high salt (8% NaCl) diet at 6 wk of age and observed until natural death. Homozygous male and female rats from two transgenic lines, lines 24 and 48, were compared to non-transgenic Dahl S controls while fed a normal rat chow diet (0.4% NaCl), and observed until natural death. Statistical analysis was done by one-way ANOVA.

Measurement of Blood Pressure by Radiotelemetry.

Blood pressure was measured using intra-aortic abdominal radiotelemetric implants (DATASCIENCE, St. Paul, Minn.) obtaining non-stressed blood pressure measurements taking the average over 10 s every 5 min for 24 h (16). The 24-h average of all data points (288) over one no-entry day at said time point after high salt challenge was used for all blood pressure measurements analyzed. The 24-h average was determined to be the best because it would account for diurnal variation, thus ascertaining accuracy. Because telemetric blood pressure signals were collected via computer, measurements were obtained without disturbance from room change, or room entry. Systolic (SBP), diastolic (DBP), and mean arterial pressures (MAP) were measured along with heart rate and activity. The protocol for transgenic and age-matched non-transgenic Dahl S rats was as follows: implant surgery at 10 wk of age; only rats with no complications after operation were used; after 12 d, baseline blood pressure levels were obtained; high salt (8% NaCl) challenge was begun at 12 wk of age and maintained for 4 wk; and transgenic and control rats were killed after 4 wk on high (8% NaCl) salt challenge (16 wk of age). The protocol for characterization of parental Dahl S and Dahl R rats, F1(S×R) and F2(S×R) hybrid rats was as follows: implant surgery at 8 wk of age; only rats with no complications after operation were used; after 12 d, baseline blood pressures were obtained; and high (8% NaCl) salt challenge was begun at 10 wk of age with water ad libitum. After 8 wk of high (8% NaCl) salt challenge, 24-h average SBP, DBP, MAP, and increment rise in 24-h average of SBP, DBP, and MAP were obtained per rat over one no-entry day (288 data points, 10-s recordings every 5 min).

Assessment of Renal Pathology.

Renal tissues were fixed in 4% buffered paraformaldehyde and processed at HistoTechniques (Ohio). Serial renal sections were stained using hematoxylin-eosin, periodic acid Schiff(PAS), and Masson Trichrome stain. All glomeruli in one renal section (5 μm) were analyzed for degree of glomerulosclerosis and mesangial matrix expansion. Age-matched control non-transgenic and transgenic male and female rats were studied after 4 wk of high salt diet challenge. Glomerulosclerosis was defined as disappearance of cellular elements from the tuft, collapse of capillary lumen, and folding of the glomerular basement membrane with entrapment of amorphous material (18). Mesangial matrix expansion was defined by the presence of increased amounts of PAS-positive material in the mesangial region (18). Renal pathology grade I, 25% of glomerulus with pathology; II, 50% involvement; III, 75% involvement; IV, 100% involvement. The extent of injury for each renal section was calculated, as the total pathology score=(1×% grade I)+(2×% grade II)+(3×% grade III)+(4×% grade IV), increasing with worse injury represented by glomerulosclerosis and mesangial matrix expansion (18). Renal sections were scored in a blind manner. Data were analyzed using non-parametric ANOVA.

Cosegregation Analysis.

The F2 cohort was derived from one Dahl S male and six Dahl R female rats from HSD colonies previously verified for genotype and phenotype (19). Non-stressed 24-h average blood pressure measurements were obtained by radiotelemetry, as described above. After 8 wk of high salt challenge, the F2 hybrid rats were killed and tail genomic DNAs isolated as described (16). Genotyping was performed using the following microsatellite markers: D2mit14; D2mgh11 (α1 Na,K-ATPase); D2mit12; D2mit10; CAMK, and D2mit6 (14) informative for our Dahl S×Dahl R cross. Nine other markers (D2 mgh14, D2mit5, CPB, D2mit17, D2 mgh15, D2mit13, D2mit20, D2 mgh12, and D2mit5) (14) were also investigated but were found to be non-polymorphic in our cross. Correlation of blood pressure parameters and genotypes for the different chromosome 2 markers was analyzed by one-way ANOVA (SigmaStat; Jandel Scientific, San Rafael, Calif.). Correction for multiple comparisons was not done, as parameters studied are closely related phenotypes.

EXAMPLE 2

Ascertainment of Genotype and phenotype of Dahl S and Dahl R Strains.

Due to the inadvertent genetic contamination of Dahl S rats at the sole commercial source resulting in subsequent contamination, the first transgenic lines were all terminated. To perform transgenic and cosegregation studies in non-contaminated Dahl S rats, collaboration was set up with Harlan Sprague Dawley, Inc. (19) to identify non-contaminated Dahl $S^{HSD}$ rats. In 1994, experiments were begun to ascertain non-contaminated genotype and salt-sensitive hypertension phenotype of the Dahl $S^{HSD}$ foundation colony, and, in parallel, the inbred genotype and salt-resistance phenotype of Dahl $R^{HSD}$ rats.

FIG. 1 shows the genetic analysis of Dahl $S^{HSD}$ rats. (A) Genotyping with contamination-indicative markers (20) corroborates non-genetic contamination of Dahl $S^{HSD}$ foundation colony rats. A representative panel is shown for the R80 marker (20) demonstrating non-heterozygosity among Dahl $S^{HSD}$ and Dahl $R^{HSD}$ foundation colony rats; non-heterozygosity was detected in all contamination-indicative (20) markers. The respective sizes of amplified product were: Dahl S Dahl R with R1041, R138, and R80 markers; Dahl S=Dahl R with R721 GCA, R354. (B) PASA detection of $T^{1079}$/A transversion in Dahl $S^{HSD}$ rat genomic DNA corroborates Q276L α1 Na,K-ATPase mutation. Comparing two Dahl R(R) and two Dahl S(S) rat genomic DNA samples, PASA analysis using primer-specific for T1079 detects significantly more amplified product in Dahl S rat samples (arrow) compared with Dahl R(R) rat genomic DNA samples at 57° C. Background amplified products could be expected as PASA detects a single base difference. As control, a non-specific marker, Cype (14), was used to indicate relative amounts of genomic DNA in the different samples (arrowhead). Taking the ratio of PASA-product to Cype-amplified product, Dahl S samples exhibit ratios>1; whereas Dahl R samples exhibit ratios<1. These results indicate the presence of $T^{1079}$ in Dahl S rat genomic DNA corroborating the Q276L α1 Na,K-ATPase variant as previously described (8, 9).

Using six microsatellite markers informative for the reported genetic contamination (20), foundation colony Dahl $S^{HSD}$ and Dahl $R^{HSD}$ rats were checked; no heterozygosity was detected (FIG. 1A). Blood pressure phenotypes of foundation colony Dahl $S^{HSD}$ and Dahl $R^{HSD}$ rats were ascertained using radiotelemetric blood pressure measurements on a high salt (8% NaCl) diet begun at 10 wk of age. Severe salt-sensitive hypertension was detected in male and female Dahl S rats in contrast to salt-resistant normotension in male and female Dahl R rats. The data parallel the blood pressure phenotypes reported in the original Dahl S/JR and Dahl R/JR characterization (21). Only after this ascertainment were non-contaminated Dahl $S^{HSD}$ and Dahl $R^{HSD}$ rats obtained for transgenic experiments begun in 1995. Random testing of transgenic donor female and male Dahl S rats further corroborated absence of genetic contamination.

Additionally, genotyping analysis using a panel of 97 microsatellite markers informative for Dahl S and Dahl R strains and eight markers identical in Dahl S and R strains (14, 22) was done comparing Dahl $S^{HSD}$ and Dahl $R^{HSD}$ rats used for our experiments, with Dahl $S^{Rapp}$ rats obtained by Harlan Sprague Inc. from J. Rapp (21). The results show that 103 of 105 markers were identical between Dahl $S^{HSD}$ and Dahl $S^{Rapp}$ rats; differences were noted at two markers (D1mgh7 and D2mit5); heterozygosity was detected in the Dahl $S^{Rapp}$ rats at D2mit13. These results document the non-genetic contamination of Dahl $S^{HSD}$ and acceptable polymorphic differences between Dahl $S^{HSD}$ and Dahl $S^{Rapp}$ due to separate inbreeding over two decades.

Figure 1B:
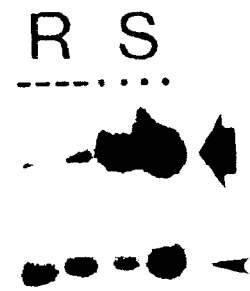

Furthermore, we corroborated once again the presence of Q276L mutation in Dahl $S^{HSD}$ and its absence in Dahl R $rat^{HSD}$ genomic DNA by error-independent PCR allele-specific amplification (PASA) detecting $T^{1079}$ in Dahl S, in contrast to non-$T^{1079}$ in Dahl R genomic DNA (FIG. 1B). This corroborates previous PASA results (9). However, we note that sequencing of a Dahl S α1 Na,K-ATPase genomic DNA fragment encompassing amino acid 276 isolated from a Fix II Dahl $S_{HSD}$ rat genomic library did not detect the $A^{1079}$T transversion underlying the Q276L mutation. In light of the consistent PASA results detecting the Q276L variant-specific $T^{1079}$ genomic DNA and previous observations demonstrating that PCR amplification reproducibly changed the Dahl S variant $T^{1079}$ to $A^{1079}$ (9), it becomes apparent that amplification of this genomic DNA region is indeed $[T^{1079}-A^{1079}]$-specific error prone.

EXAMPLE 3
Development of Dahl S Transgenic Rat Lines

Based on observations that male and female F1(Dahl S×Dahl R) rats have blood pressures closer to the Dahl R rat strain after 8 wk of high salt (8% NaCl) diet, it becomes apparent that SS-EHT in the Dahl S rat model is recessive. Accordingly, a robust transgenic design should involve the transfer of Dahl R wt Q276 1 Na,K-ATPase gene into the Dahl S genetic background, testing its effects on salt-sensitive hypertension phenotype.

FIG. 2 shows the molecular characteristics of transgenic Tg[wtα1] lines. (A) The transgene construct, Tg[wtα1], is comprised of [1288 bp] of wt α1 Na,K-ATPase 5' flanking regulatory region (wt α1 promoter), linked to wt (Q276) α1 Na,K-ATPase cDNA: spanning the entire 206-bp 5' untranslated region, full length 1,028-amino acid-coding region, and 131 bp of 3' untranslated region; linked to 199 bp of SV40 polyadenylation signal. (B) Southern blot analysis of transgenic F1 hemizygous Dahl S rats representing the three founder lines, Tg[wtα1]$_{37}$ (lane 1); Tg[wtα1]$_4$s (lane 2); Tg[wtα1]$_{24}$ (lane 3), control non-transgenic Dahl S rat DNA (lane 4). M, Hind III molecular weight markers from top to bottom: 23,130 bp; 9,416 bp; 6,557 bp; and 4,361 bp. As shown on the left, SacI digested genomic DNA reveals intact Tg[wtα1] transgene (4.657-kb fragment at closed arrow) detected only in the transgenic rats (lanes 1–3) and not in the non-transgenic control (lane 4). Other hybridizing SacI DNA fragments (arrowhead) in lane 1, ~7 kb; lane 2, ~24 kb; and lane 3, ~9.5 kb, indicate different random integration sites of the transgene into the genome. Additionally, different copy numbers are evident: Tg[wtα1]$_{48}$ (lane 2)>Tg[wtα1]$_{24}$ (lane 3)>Tg[wtα1]$_{37}$ rat (lane 1). On the right, HindIII restriction digestion reveals the intact transgene (closed arrow) with a>30-kb fragment in the transgenic rat lines, absent in control (lane 4). The endogenous α1 Na,K-ATPase HindIII fragment is smaller, ~30 kb (open arrow), and is detected in transgenic and control non-transgenic rat genomic DNA. (C) The composition of the RPA probe used to assess wt (transgene) and Q276L variant (endogenous) α1 Na,K-ATPase RNA levels is presented: a 310-nt RPA probe comprised of 131 bp of 3' untranslated (UT) region of the α1 Na,K-ATPase cDNA present in both transgene and endogenous α1 Na,K-ATPase, linked to 109 bp of SV40 sequence, which is present only in the transgene; and 70-bp vector sequence. The transgene wt α1 Na,K-ATPase RNA is expected to be 240-nt-long, distinguished from the endogenous Q276L variant α1 Na,K-ATPase RNA, expected to be 131-nt long. (D) RPA of total cellular RNA from heart (lanes 1 and 2), brain (lanes 3 and 4), and kidney (lanes 5 and 6) of homozygous transgenic Tg[wtα1] (lanes 2, 4, and 6) and control non-transgenic (lanes 1, 3, and 5) Dahl S rats. (–), control yeast RNA; $^{32}$P, RPA radiolabeled probe; m, molecular size markers in base pairs from top to bottom: pBR322 DNA-MspI digest: 404, 307, 242, 238, 217, 201, 190, 180, 160, 147, 123, 110 bp. (E) RPA of total aortic RNA from homozygous transgenic (lanes 4 and 5) and age-matched control (lanes 1, 2, and 3) non-transgenic Dahl S rats. (F) Longer exposure (10×) of E. (closed arrow), 240-nt protected fragment indicative of wt transgene α1 Na,K-ATPase mRNA; (open arrow), partial protection 131-nt fragment, indicative of endogenous Q276L variant α1 Na,K-ATPase mRNA. (G) Assessment of wt (transgene) and Q276L variant (endogenous) α1 Na,K-ATPase RNA levels in membrane-bound polysomes of homozygous Tg[wtα1] rats. The identical RPA probe (shown in C) was used to perform RNAse protection assays (RPA) on membrane-bound polysomal RNA isolated from homozygous Tg[wtα1]24 Dahl S rat kidney (lane 1). 32P, RPA probe; m, molecular size markers in base pairs from top to bottom: pBR322 DNA-MspI digest: 404, 307, 242, 238, 217, 201, 190, 180, 160, 147 bp. Top (arrowhead), 240-nt protected fragment indicative of wt transgene α1 Na,K-ATPase mRNA; bottom (arrowhead), partial protection 131-nt fragment, indicative of endogenous Q276L variant α1 Na,K-ATPase mRNA.

Figure 2A:
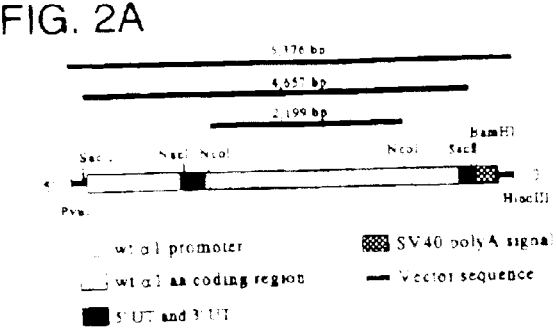
FIGS. 2A–2G show molecular characteristics of transgenic Tg[wtα1] lines.
Figure 2B:
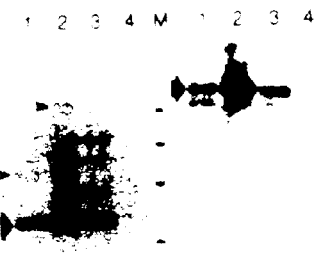
Figure 2C:
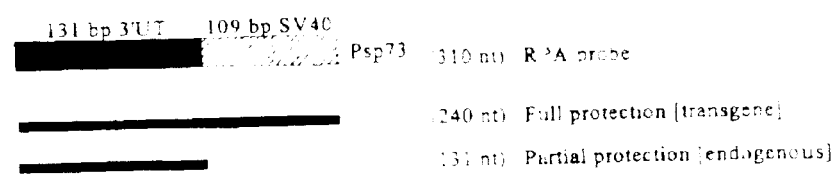

To attain appropriate spatial and developmental gene regulation, the transgene design links the cognate wt α1 Na,K-ATPase promoter region, functionally validated previously (15); the Dahl R wt α1 Na,K-ATPase cDNA (8, 9); and SV40 polyadenylation signal sequences, Tg[wtα1] (FIG. 2A). Transgenic rats were developed as described (16). Three transgenic lines were developed, Tg[wtα1]$_{24, 37, and 48}$. Southern blot analyses revealed intact transgene sequences in all three transgenic lines showing the predicted 2.199-kb NcoI fragment, the predicted 4.657-kb SacI fragment (FIG. 2B), and HindIII restriction digestion fragments greater than the microinjected 5.376-kb transgene recombinant construct hybridizing to the α1 Na,K-ATPase cDNA probe (FIG. 2B). Different copy numbers are also noted. Other restriction fragments hybridizing to the α1 Na,K-ATPase cDNA probe are detected in both control and transgenic rat DNAs representing the endogenous α1 Na,K-ATPase gene (FIG. 2B).

To gain insight into the relative ratio of expression of the endogenous Q276L variant versus the transgene wt α1 Na,K-ATPase, RPAs were done (FIG. 2, C–F). The endogenous Q276L α1 Na,K-ATPase variant is detected as the expected 131-nt-long partial protection fragment (FIG. 2C) in both control (odd numbered) and transgenic (even numbered) rat RNA samples (FIG. 2D): heart (lanes 1 and 2), brain (3 and 4), and kidney (5 and 6). The endogenous-specific 131-nt-long fragment is likewise detected in aorta on short (FIG. 2E) and longer exposure (FIG. 2F). The relative levels detected are consistent with spatial expression patterns in the rat (6). In contrast, the transgene-specific α1Na,K-ATPase expected 240-nt protected fragment (FIG. 2C) is detected only in transgenic rat tissue RNA samples as shown in FIG. 2D: lane 2, heart; lane 4, brain; lane 6, kidney; and FIG. 2E, lanes 4 and 5, FIG. 2F, lanes 4 and 5, aorta. It should be noted that the total amount of α1 Na,K-ATPase transcript is not dramatically increased by the level of transgene expression in both transgenic lines with Tg[wtα1]$_{24}$ exhibiting higher expression levels compared with Tg[wtα1]$_{48}$, transgenic line.

Figure 2D:
Figure 2E:
Figure 2F:
Figure 2G:
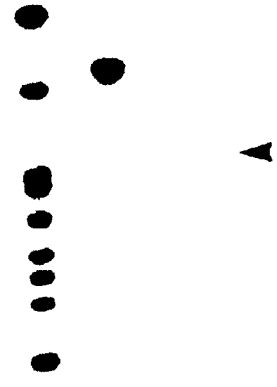

To determine the membrane-integrated relative protein levels of transgene-to-endogenous α1 Na,K-ATPases in the absence of an informative antibody, assessment of their respective relative levels was determined in the renal translational pool compartmentalized to kidney membrane-bound polysomes of homozygous transgenic Tg[wtα1] Dahl S rats. This was done by RPA analysis of membrane-bound polysomal RNA isolated from a homozygous transgenic Tg[wtα1] Dahl S rat kidney using the same probe depicted in FIG. 2C. As shown in FIG. 2G, the 240-nt protected fragment representing the transgene wt α1Na,K-ATPase transcript is almost equivalent in amount to the 131-nt-long protected fragment representing the endogenous Q276L variant α1 Na,K-ATPase transcript (~40:60 ratio of transgene wt α1 Na,K-ATPase to endogenous Q276L variant α1 Na,K-ATPase). This is in marked contrast to the underrepresentation of the transgene wt RNA in the total cellular pool (FIG. 2D). Although the precise mechanism that could account for this differential representation, is as yet unclear, it is likely that structural differences within the 3'UT between the wt (transgene) and Q276L variant (endogenous) mRNAs could account in part for their differential RNA stability when compartmentalized to the non-translational pool.

EXAMPLE 4

Alleviation of Salt-Sensitive Hypertension Phenotype

To test whether Tg[wtα1] transgene expression modifies the salt-sensitive hypertension phenotype of inbred Dahl S rats, we analyzed three parameters: (a) life span on a high salt (8% NaCl) and on regular (0.4% NaCl) rat chow, (b) blood pressure levels, and (c) hypertensive renal disease. A priori, concordance of effects in all three parameters would strongly indicate a bona fide mechanistic role for α1 Na,K-ATPase. Life span was analyzed in hemizygous transgenic rats challenged with a high salt (8% NaCl) diet at six wk of age.

FIG. 3 shows the life span in hemizygous and homozygous transgenic Tg[wtα1] Dahl S rats compared with control non-transgenic Dahl S rats. (A) Hemizygous male and female transgenic rats from the three Tg[wtα1] lines on high salt (8% NaCl) diet begun at 6 wk of age lived longer (13.0±0.5 wk; n=23) than control littermate non-transgenic (11.4±0.4 wk; n=19) Dahl S rats (P<0.01, one-way ANOVA). (B) Homozygous male and female Tg[wtα1]$_{24}$ and Tg[wtα1]$_{48}$, rats on regular (0.4% NaCl) rat diets lived longer (54.8±2.3 wk; n 10), compared with non-transgenic control Dahl S rats (31.2±1.2 wk; n=19); P<10–9, one-way ANOVA.

Figure 3A:
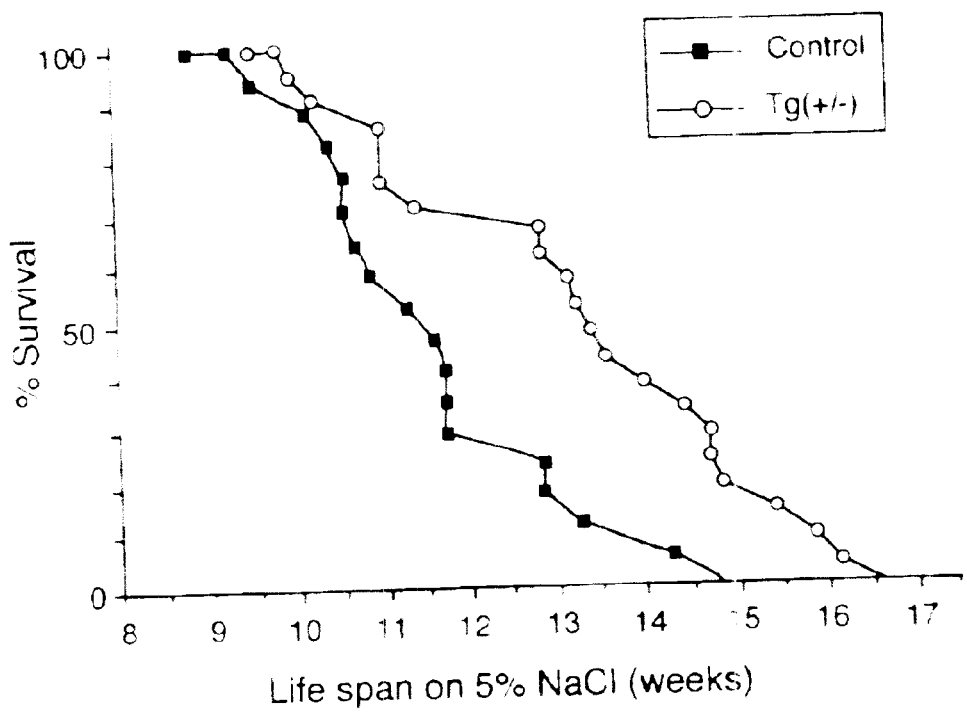
FIGS. 3A–3B show life span in hemizygous and homozygous transgenic Tg[wtα1] Dahl S rats compared with control non-transgenic Dahl S rats.
Figure 3B:
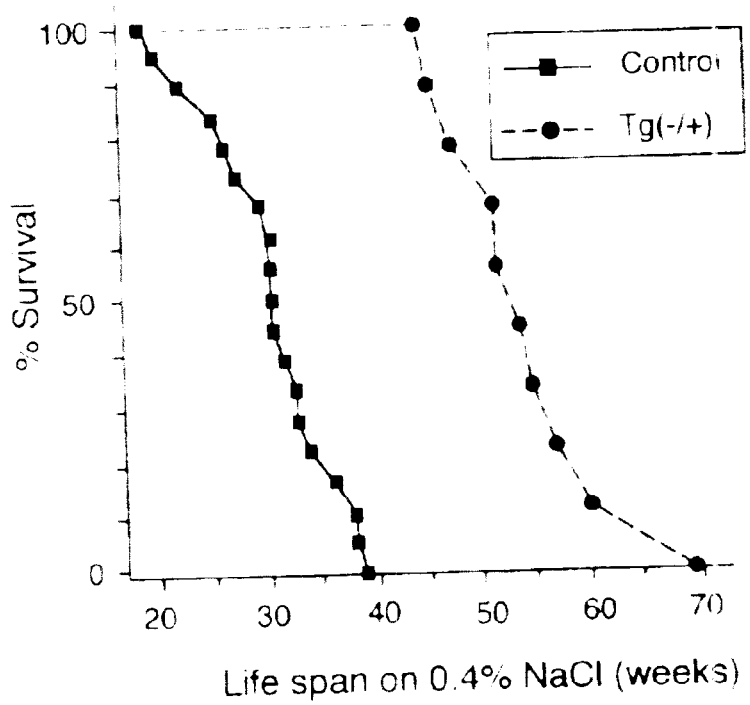

As seen in FIG. 3A, hemizygous male and female rats from three transgenic lines lived longer than littermate non-transgenic Dahl S rat controls. Mean life span of hemizygous Tg[wtα1] rats (13.0±0.5 wk, n=23) increased 14% compared with controls (11.4±0.4 wk, n=19), P<0.01 one-way ANOVA. Upon successfully breeding Tg[wtα1]$_{24}$ and Tg[wtα1]$_{48}$ lines to homozygosity, life span was analyzed on a regular (0.4% NaCl) rat chow. As seen in FIG. 3B, male and female homozygous rats lived longer than control non-transgenic Dahl S rats. Mean life span of homozygous Tg[wtα1]$_{24,48}$ rats (54.8±2.3 wk, n=10) increased 75.6% compared with controls (31.2±1.2 wk, n=19), P<10-9 by one-way ANOVA. Improvement in mortality suggested that salt-sensitive hypertension phenotype was most likely alleviated in the different transgenic rat lines.

Blood pressure measurements were then analyzed comparing homozygous male and female transgenic Tg[wtα1]$_{24}$ rats with non-transgenic age-matched Dahl S control rats. Group means of 24-h SBP, DBP, and MAP levels in both male and female transgenic Tg[wtα1]$_{24}$ rats were consistently lower than blood pressure levels detected in age-matched control non-transgenic Dahl S rats. Likewise, the levels of increment rise in blood pressure parameters, SBP, DBP, and MAP, after 4 wk of high salt challenge were also significantly lower in both male and female transgenic Tg[wtα1]$_{24}$ rats.

To assess potential improvement in EHT-induced target organ damage, comparison of PAS-stained renal sections from five transgenic rat kidneys representing homozygous transgenic Tg[wtα1]$_{24}$ and Tg[wtα1]$_{48}$ rats and from four control non-transgenic rat kidneys was done. Low magnification revealed significant differences between transgenic rat kidney sections and control non-transgenic rat kidney sections. No differences were noted between sexes.

FIG. 4 shows the comparative analysis of degree of hypertensive renal disease. Representative PAS-stained renal sections of non-transgenic Dahl S rat kidney (A) show more severe renal pathology after 4 wk of high salt diet compared with age-matched transgenic Dahl S rat kidney (B). Low power magnification reveals more hyaline casts and abnormal glomeruli with intensely PAS-positive mesangial thickening and glomerulosclerosis per unit area in non-transgenic rat kidney section (A) compared with transgenic rat kidney section (B). Abnormal glomeruli with grade IV Raij pathology score lesions are marked (arrowhead). C, D, E, F, and G show high power magnification demonstrating different grades of glomerular pathology used as parameters for quantitation of extent of renal pathology based on the Raij pathology score (18). (C) normal glomerulus; (D) grade I glomerular pathology with mesangial thickening and/or glomerulosclerosis covering 25% of glomerulus; (E) grade II glomerular pathology involving 50% of glomerulus; (F) grade III glomerular pathology involving 75% of glomerulus; (G) grade IV glomerular pathology, 100% involvement. Calculation of the total pathology score=[1(% grade I)+2(% grade II)+3(% grade III)+4(% grade IV)] indicates worse renal pathology with increasing scores.

As shown in FIG. 4, a greater number of magenta PAS-positive abnormal glomeruli are seen in a representative control rat kidney section (FIG. 4A) compared with a representative transgenic kidney section (FIG. 4B), indicating less hypertensive renal disease in transgenic rats. This was corroborated by quantitative analysis of renal pathology based on the scoring system described by Raij et al. (18), wherein glomeruli are graded for degree of mesangial thickening and glomerulosclerosis. As shown in FIG. 4, a glomerulus with 25% mesangial thickening and/or glomerulosclerosis is grade I (FIG. 4D); grade II is 50% pathologic involvement (FIG. 4E); grade III, 75% involvement (FIG. 4F); and grade IV, 100% pathologic involvement (FIG. 4G), in contrast to a normal glomerulus (FIG. 4C). A total pathology score is calculated with worse severity correlated with higher pathology scores (18). Analysis of renal sections from four control non-transgenic rats (628 total glomeruli scored) compared with five transgenic rat kidney sections (1,213 total glomeruli scored) for severity of mesangial thickening and glomerulosclerosis revealed a 52% decrease in Raij renal pathology score in transgenic rat kidneys compared with control rat kidneys, P=0.0025 (non-parametric ANOVA).

This decrease in renal pathology in transgenic Tg[wtα1] Dahl S rats is consistent with the observed improvement in life span and the alleviation of SS-EHT. More importantly, the concordance of improvement in three measures, life span, blood pressure, and hypertensive renal disease, as well as the 40:60 transgene: endogenous α1 Na,K-ATPase ratio provide evidence to meet our third criteria for the role of the α1 Na,K-ATPase gene in SS-EHT.

EXAMPLE 4

Intercross Linkage Analysis.

To fulfill criterion 4, cosegregation analysis was done on fifty F2(S×R) hybrid male rats phenotyped for SBP, DBP, MAP, heart rate, and activity by radiotelemetry at baseline (10 wk of age) and after 8 wk of high (8% NaCl) salt challenge. These 50 F2 rats were genotyped at 15 markers that spanned chromosome 2 (14). ANOVAs comparing phenotypes across the three genotypic categories for each informative marker locus (6 out of 15) were carried out.

Figure 5:
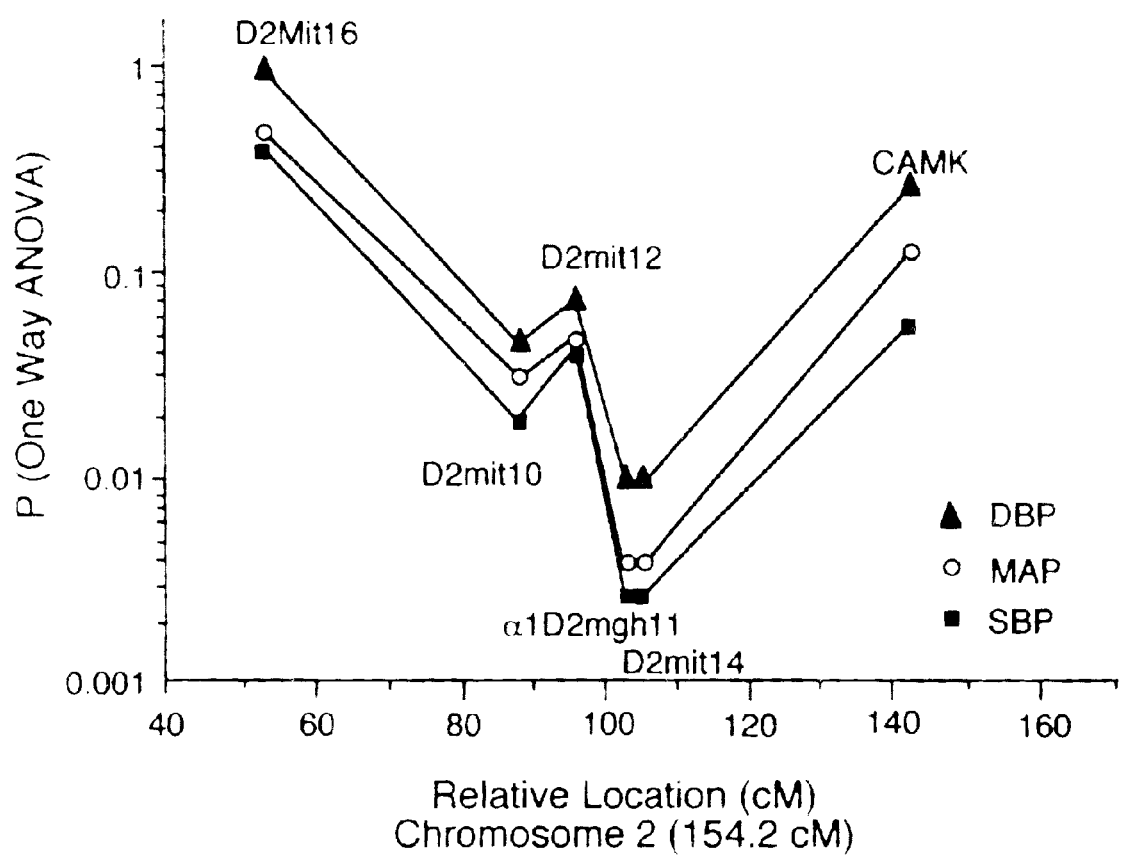
FIG. 5 shows the cosegregation analysis of $\alpha 1$ Na,K-ATPase locus with salt-sensitive hypertension.

FIG. 5 shows cosegregation analysis of the α1 Na,K-ATPase locus with salt-sensitive hypertension. Total chromosome 2 scan analyzing marker cosegregation with salt-sensitive hypertension in an F2(Dahl S×Dahl R) cohort (n=50 males) measured as increment rise in 24-h average systolic (SBP), diastolic (DBP) and mean arterial pressures (MAP) obtained after 8 wk of high (8% NaCl) salt diet. Markers informative for the Dahl S and R hybrid cross are marked along their respective relative location on chromosome 2 in centimorgans (cM) based on the rat map (14). Greatest significance is seen with the α1 Na,K-ATPase locus (D2 mgh11marker) and the D2mit14 marker, <2.2 cM away. In contrast to other studies (22), D2mit12 and CAMK markers do not cosegregate with salt-sensitive hypertension. Correlation trends along chromosome 2 are parallel for SBP, DBP, and MAP.

As seen in FIG. 5, the most significant ANOVA results were detected at the α1 Na,K-ATPase locus (D2 mgh11) and at the D2mit14 marker, 2.2 centimorgans (cM) away, for SBP (P=0.00268), DBP (P=0.00920), MAP (P=0.00376). The fact that all three blood pressure measures provide similar results is in contrast to other F2 cosegregation studies that have detected cosegregation with one blood pressure parameter but not with the others, e.g., locus cosegregation with DBP and pulse pressure, but not with SBP or MAP (23). These results indicate that the α1 Na,K-ATPase locus meets criterion 4.

REFERENCES

1. Herrera, V. L. M., and N. Ruiz-Opazo (1991) Genetics of hypertension: a multidisciplinary challenge. Trends Cardiovasc. Med 1: 185–189.
2. Herrera, V. L. M., and N. Ruiz-Opazo (1994) Beyond genetic markers: hypertension genes. J. Hypertension. 12: 847–856.
3. Dahl, L. K, M. Heine, and L. Tassinari (1972) Role of genetic factors in susceptibility to experimental hypertension due to chronic excess salt ingestion. Nature. 194: 480–482.
4. Dahl, L. K., M. Heine, and K. Thompson (1974) Genetic influence of the kidneys on blood pressure: evidence from chronic renal homografts in rats with opposite predispositions to hypertension. Circ. Res 34: 94–101.
5. Vander, A. J. 1991. Renal Physiology. 4th edition. McGraw-Hill, Inc. New York. 83-111.
6. Herrera, V. L. M., T. Cova, D. Sassoon, and N. Ruiz-Opazo (1994) Developmental cell-specific regulation of 1, 2, and 3 Na,K-ATPase gene expression. Am. J. Physiol 266: C1301–C1312.
7. DeWardener, H. E. (1990) The primary role of the kidney and salt intake in the aetiology of essential hypertension, part II. Clin. Sci 79: 289–297.
8. Herrera, V. L. M., and N. Ruiz-Opazo (1990) Alteration of 1 Na,K- ATPase 86R+influx by a single amino acid substitution. Science. 249: 1023–1026.
9. Ruiz-Opazo, N., F. Barany, K. Hirayama, and V. L. M. Herrera (1994) Confirmation of mutant 1 Na,K-ATPase gene and transcript in Dahl salt-sensitive/JR rats. Hypertension. 24: 260–270.
10. Simonet, L., E. St. Lezin, and T. W. Kurtz (1991) Sequence analysis of the 1 Na,K-ATPase gene in the Dahl salt-sensitive rat. Hypertension. 18: 689–693.
11. Schull, G. E., J. Greeb, and J. B. Lingrel (1989) Molecular cloning of three distinct forms of the Na,K-ATPase-subunit from rat brain. Biochemistry. 25: 8125–8132.
12. Canessa, M., J. R. Romero, N. Ruiz-Opazo, and V. L. M. Herrera (1993) The 1 Na,K pump of the Dahl salt-sensitive rat exhibits altered Na+ modulation of K+ transport in red blood cells. J. Membr. Biol 134: 107–122.
13. Orosz, D. E., and U. Hopfer (1996) Pathophysiologic consequences of changes in the coupling ratio of Na,K-ATPase for renal sodium reabsorption and its implications for hypertension. Hypertension. 27: 219–227.
14. Jacob, H.J., Brown, D. M. Bunker, R. K. Daly, M. J. Dzau, V. J. Goodman, A. Koike, G. Kren, V. Kurtz, T. Lermnark, et αl (1995) A genetic linkage map of the laboratory rat, Rattus norvegicus. Nat. Genet. 9: 63–69.
15. Ruiz-Opazo, N., J. F. Cloix, M. G. Melis, X. H. Xiang, and V. L. M. Herrera (1997) Characterization of a sodium-response transcriptional mechanism. Hypertension. 30: 191–198.
16. Ruiz-Opazo, N., X. H. Xiang, and V. L. M. Herrera (1997) Pressure-overload deinduction of human 2 Na,K-ATPase gene expression in transgenic rats. Hypertension. 29: 606–612.
17. Dallner, G. 1974. Isolation of rough and smooth microsomes —general. In Methods in Enzymology, Vol. XXXI, S. Fleischer and L. Packer, editors. Academic Press, New York. 191-201.
18. Raij, L., S. Azar, and W. K. Keane (1984) Mesangial immune injury, hypertension, and progressive glomerular damage in Dahl rats. Kidney Int 26: 137–143.
19. Herrera, V. L. M., R. J. Russell, Q. Fang, J. R. McGinley, and N. Ruiz-Opazo (1995) Genotypic and phenotypic characterization of inbred Dahl salt-sensitive (SS/JR Hsd) and salt-resistant (SR/JRHsd) rats. Contemp. Top. 34: 51
20. Lewis, J. L., R. J. Russell, and D. G. Warnock (1994) Analysis of the genetic contamination of salt-sensitive Dahl/Rapp rats. Hypertension. 24: 255–259.
21. Rapp, J.P., and H. Dene (1985) Development and characteristics of inbred strains of Dahl salt-sensitive and salt-resistant rats. Hypertension. 7: 340–349.
22. Deng, A. Y., H. Dene, and J. P. Rapp (1994) Mapping of a quantitative trait locus for blood pressure on rat chromosome 2. J. Clin. Invest 94: 431–436.
23. Dubay, C., M. Vincent, N. J. Samani, P. Hilbert, M. A. Kaiser, J.P. Beressi, Y. Kotelevtsev, J.S. Beckmann, F. Soubrier, J. Sassard, and G.M. Lathrop (1993) Genetic determinants of diastolic and pulse pressure map to different loci in Lyon hypertensive rats. Nat. Genet. 3: 354–357.
24. St. Lezin, E. M., M. Pravenec, A. Wong, J.-M. Wang, T. Merriouns, S. Newton, D. E. Stec, R. J. Roman, D. Lau, R. C. Morris, and T. W. Kurtz (1994) Genetic contamination of Dahl SS/JR rats: impact on studies of salt-sensitive hypertension. Hypertension. 23: 786–790.
25. Clark, J. S., B. Jeffs, A. O. Davidson, W. K. Lee, N. H. Anderson, M. T. Bihoreau, M.J. Brosnan, A.M. Devlin, A.W. Kelman, K. Lindpaintner, and A.F. Dominiczak (1996) Quantitative trait loci in genetically hypertensive rats. Hypertension. 28: 898–906.
26. Samani, N.J., D. Gauguier, M. Vincent, M. A. Kaiser, M. T. Bihoreau, D. Lodwick, R. Wallis, V. Parent, P. Kimber, F. Rattray, etαl (1996) Analysis of quantitative trait loci for blood pressure on rat chromosomes 2 and 13. Hypertension. 28: 1118–1122.
27. Lander, E., and L. Kruglyak (1995) Genetic dissection of complex traits: guidelines for interpreting and reporting linkage results. Nat. Genet. 11: 241–247.
28. National Heart, Lung and Blood Institute Report of the Task Force on Research in Hypertension. United States Department of Health and Human Services. May 1991.
29. Goldman, D. (1996) High anxiety. Science. 274: 1483.
30. Lesch, K. P., D. Bengel, A. Heils, S. Z. Sabol, B. D. Greenberg, S. Petri, J. Benjamin, C. R. Muller, D. H. Harer, and D. L. Murphy (1996) Association of anxiety-related traits with a polymorphism in the serotonin transporter gene regulatory region. Science. 274: 1527–153 1.
31. Lander, E., and N. J. Schork (1994) Genetic dissection of complex traits. Science. 265: 2037–2048.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of assaying a test compound for an effect on hypertension parameters, said method comprising:
   (a) providing a Dahl Salt-sensitive[HSD] rat whose genome comprises a functional variant α1 Na,K-ATPase hypertension susceptibility gene;
   (b) administering said test compound to said rat; and
   (c) determining whether the test compound affects hypertension parameters in said rat relative to hypertension parameters in a rat whose genome comprises a wild type α1 Na,K-ATPase gene.

2. The method of claim 1, wherein said hypertension parameters are blood pressure, life span, or renal pathology.

* * * * *